United States Patent
Sookraj

(10) Patent No.: US 10,961,209 B2
(45) Date of Patent: Mar. 30, 2021

(54) PROCESSES FOR PRODUCING BETA-LACTONE AND BETA-LACTONE DERIVATIVES WITH HETEROGENOUS CATALYSTS

(71) Applicant: Novomer, Inc., Boston, MA (US)

(72) Inventor: Sadesh H. Sookraj, Cambridge, MA (US)

(73) Assignee: Novomer, Inc., Rochester, NY (US)

( * ) Notice: Subject to any disclaimer, the term of this patent is extended or adjusted under 35 U.S.C. 154(b) by 0 days.

(21) Appl. No.: 16/057,530

(22) Filed: Aug. 7, 2018

(65) Prior Publication Data

US 2019/0047972 A1 Feb. 14, 2019

Related U.S. Application Data

(63) Continuation-in-part of application No. 15/674,453, filed on Aug. 10, 2017, now Pat. No. 10,590,099.

(51) Int. Cl.
| | | |
|---|---|---|
| *C07D 305/12* | (2006.01) | |
| *C07D 407/12* | (2006.01) | |
| *C07D 305/14* | (2006.01) | |
| *B01J 37/08* | (2006.01) | |
| *B01J 37/02* | (2006.01) | |
| *B01J 29/46* | (2006.01) | |

(52) U.S. Cl.
CPC ............ *C07D 305/12* (2013.01); *B01J 29/46* (2013.01); *B01J 37/024* (2013.01); *B01J 37/0207* (2013.01); *B01J 37/0236* (2013.01); *B01J 37/086* (2013.01); *C07D 305/14* (2013.01); *C07D 407/12* (2013.01)

(58) Field of Classification Search
CPC .................................................. C07D 305/12
See application file for complete search history.

(56) References Cited

U.S. PATENT DOCUMENTS

| | | |
|---|---|---|
| 3,885,155 A | 5/1975 | Anbar |
| 4,127,249 A | 11/1978 | Lambregts |
| 4,187,168 A | 2/1980 | McVicker |
| 4,192,777 A | 3/1980 | McVicker et al. |
| 4,271,302 A | 6/1981 | McVicker |
| 4,427,884 A | 1/1984 | Anbar |
| 4,472,517 A | 9/1984 | Tsao et al. |
| 4,613,624 A | 9/1986 | Beuther et al. |
| 4,973,841 A | 11/1990 | Purser |
| 5,256,828 A | 10/1993 | Cuscurida |
| 5,310,948 A | 5/1994 | Drent |
| 5,359,081 A | 10/1994 | Drent |
| 5,438,194 A | 8/1995 | Koudijs |
| 5,661,299 A | 8/1997 | Purser |
| 6,852,865 B2 | 2/2005 | Coates |
| 7,420,064 B2 | 9/2008 | Luinstra |
| 8,445,703 B2 | 5/2013 | Allen et al. |
| 10,590,099 B1 * | 3/2020 | Sookraj ............. B01J 37/0201 |
| 2005/0014977 A1 | 1/2005 | Drent |
| 2007/0161806 A1 | 7/2007 | Preishuber-Pflugl |
| 2014/0309399 A1 | 10/2014 | Porcelli et al. |
| 2017/0029352 A1 | 2/2017 | Sookraj et al. |
| 2018/0029005 A1 | 2/2018 | Sookraj |

FOREIGN PATENT DOCUMENTS

| | | | |
|---|---|---|---|
| WO | 2010118128 | 10/2010 | |
| WO | WO-2010118128 A1 * | 10/2010 | ........... C07D 305/12 |
| WO | 2013063191 | 5/2013 | |
| WO | WO-2013063191 A1 * | 5/2013 | ........... C08G 63/823 |
| WO | 2009155086 | 10/2013 | |

OTHER PUBLICATIONS

Tamara L. Church, Yulan D.Y.L. Getzler, Christopher M. Byrne, Geoffrey W. Coates, Chem. Commun., 2007, 657-674.
Kegel, W., et al. "The Immobilization of a Transfer Hydrogenation Catalyst on Colloidal Particles," ChemCatChem. (2017), vol. 9, pp. 440-450.
International Search Report in co-pending International Application No. PCT/US2019/044823 dated Oct. 25, 2019 (8 pages).

* cited by examiner

*Primary Examiner* — John S Kenyon
(74) *Attorney, Agent, or Firm* — Young Basile Hanlon & MacFarlane, P.C.

(57) ABSTRACT

The present invention is directed to processes from producing beta-lactone and beta-lactone derivatives using heterogenous catalysts. In preferred embodiments of the present invention, the processes comprise the steps: passing a feed stream comprising an epoxide reagent and a carbon monoxide reagent to a reaction zone; contacting the epoxide reagent and the carbon monoxide reagent with a heterogenous catalyst to produce a beta-lactone product in the reaction zone; and removing the beta-lactone product from the reaction zone. In preferred embodiments, the heterogenous catalyst comprises a solid support containing a cationic Lewis acid functional group and a metal carbonyl compound comprising at least one of anionic metal carbonyl compound or a neutral metal carbonyl compound. In certain preferred embodiments, the epoxide reagent and carbon monoxide reagent have a biobased content.

18 Claims, No Drawings

PROCESSES FOR PRODUCING BETA-LACTONE AND BETA-LACTONE DERIVATIVES WITH HETEROGENOUS CATALYSTS

CROSS-REFERENCES OF RELATED APPLICATIONS

The present application claims benefit from U.S. application Ser. No. 15/674,453 filed Aug. 10, 2017, which is hereby incorporated by reference in its entirety as if fully restated herein.

FIELD OF THE INVENTION

This invention generally relates to processes for the improved production of beta-lactone and beta-lactone derivatives. Specifically, this invention relates to processes for carbonylation of epoxides with carbon monoxide using heterogenous catalysts. Advantageously, embodiments of the present invention may more efficiently produce beta-lactone and beta-lactone derivatives from various carbon sources including petroleum and biobased material.

BACKGROUND

For the purposes of this invention, the terms "biobased", "biobased content", and "bio-content" are used interchangeably to describe carbon atoms from biological sources, recycled sources, renewable sources, and/or otherwise sustainable sources. Carbon atoms are fundamental building blocks for many manufactured materials. Introducing biobased carbons into manufactured materials may have positive environmental effects.

The term "carbonylation" generally refers to chemical reactions that introduce carbon monoxide molecules into other organic and inorganic substrate molecules. Carbonylation results in a substrate molecule gaining a carbonyl functional group. Carbonylation reactions are important in industrial chemistry and are becoming a more important building block for fine and bulk chemicals. Conventional processes use homogenous catalysts for the carbonylation of epoxides to produce beta-lactones similar to the following reaction:

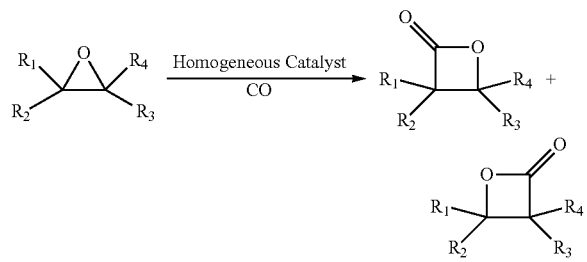

A catalyst comprises one or more atoms which may alter the rate chemical reactions and/or provide an alternative mechanism for a chemical reaction with a different transition state and/or activation energy. A homogenous catalyst, includes an atom, ion, or molecule with a particular function that is in the same phase as the reagents of a chemical reaction.

Conventional processes for carbonylation of epoxides to produce beta-lactones using homogenous catalysts may have costs associated with catalysts recycle and material recovery that could be reduced or eliminated using heterogenous catalyst systems. Certain conventional processes require the use of homogenous catalyst in a solvent. In order to reuse the catalyst, the catalyst in solvent must be passed through expensive membranes to recycle the catalyst. Conventional homogenous processes may involve the use of large volumes of solvent, hence requiring larger capacity reactors which result in higher costs associated with the size of the reactors and higher costs associated with moving large volumes of solvent through the system. Also, the processes including solvent usually require distillation resulting in extra costs associated with heating and distillation equipment.

There is a need for lower costly and more efficient processes for producing beta-lactones and beta-lactone derivatives by carbonylation of epoxides with carbon monoxide. The present invention satisfies this need with processes for carbonylation of epoxides with carbon monoxide using heterogenous catalysts.

SUMMARY OF THE INVENTION

The present invention is directed to processes for reacting the contents of a feed stream comprising an epoxide reagent and a carbon monoxide reagent with a heterogenous catalyst to produce a product stream comprising a beta-lactone product. Advantageously, the processes of the present invention have more efficient steps and eliminate certain costs associated with conventional processes for production of beta-lactones and beta-lactone derivatives.

One object of the present invention is to provide more efficient processes for production of beta-lactones and beta-lactone derivatives by reducing the utilities required to store, transfer, purify and heat solvents used in conventional processes.

Another object is to reduce the cost of materials associated with conventional processes by eliminating the need for filtration membranes, reducing or eliminating the amount of solvent used, and reducing the size of reactors necessary for production of beta-lactones and beta-lactone derivatives.

One advantage of the present invention provides for positive environmental with more efficient processes having smaller carbon footprints. Advantageously, embodiments of the present invention provide an improved life cycle assessment for beta-lactones and beta-lactone derivatives.

In preferred embodiments, the processes of the present invention overcome the deficiencies of conventional systems by providing for carbonylation of a broad range of epoxide reagents with carbon monoxide reagents to form a broad range of beta-lactones. In certain embodiments, the beta-lactones may be removed as products. In certain other embodiments, the beta-lactones may undergo further reactions to produce beta-lactone derivatives.

Preferred embodiments achieve the objects and advantages of the present invention through processes including carbonylation with a heterogenous catalyst comprising a cationic Lewis acid functional group and an anionic metal carbonyl. In certain preferred embodiments, the heterogenous catalyst comprises an organometallic compound such as a carbonyl cobaltate, a metal porphyrin compound, a metal salen compound, and/or a metal salophen compound. In certain preferred embodiments, the heterogenous catalyst may comprise a metal such as those from Groups 1 or 2 of the periodic table. In certain embodiments, the heterogenous catalyst may comprise a metal such as Ti, V, Cr, Mo, W, Mn, Tc, Re, Fe, Ru, Os, Co, Rh, Ir, Ni, or Al.

Specifically, preferred embodiments of the present invention include processes for carbonylation of epoxides with carbon monoxide using heterogenous catalysts. Embodiments of the present invention may efficiently produce beta-lactone and beta-lactone derivatives from various sources including refined petroleum sources, synthetic sources, and biobased sources.

More specifically, preferred embodiments of a process for producing a beta-lactone product from a carbon monoxide reagent and an epoxide reagent may be carried out by passing at least one of epoxide reagent to a reaction zone; passing a carbon monoxide reagent to the reaction zone; contacting at least one of epoxide reagent and the carbon monoxide reagent with a heterogenous catalyst at reaction conditions in the reaction zone to produce the beta-lactone product; and removing the beta-lactone product from the reaction zone.

Optionally in any embodiment, at least one of the epoxide reagent and the carbon monoxide reagent may be derived from renewable sources.

Optionally in any embodiment, at least one of the epoxide reagent may be selected from the group consisting of ethylene oxide, propylene oxide, 1,2-epoxyhexane, 1,2-epoxydodecane, 3,4-epoxy-1-butene, 1,2-epoxy-5-hexene, 1,2-epoxy-9-decene, isoprene monoxide, epichlorohydrin, 1,3-butadiene diepoxide, 1,2,7,8-diepoxyoctane, 1,2-epoxycyclopentane, and cyclooctene oxide.

Optionally in any embodiment, the heterogenous catalyst may comprise at least one metal carbonyl.

Optionally in any embodiment, the metal carbonyl may be selected from the group consisting of a metal porphyrin compound, a metal salen compound, and a metal salophen compound.

Optionally in any embodiment, the reaction zone may include at least one of a fixed bed reactor, a moving bed reactor, fluidized bed reactor, trickle bed reactor, catalytic distillation zone, a continuously stirred tank reactor or a tubular reactor.

Optionally in any embodiment, the reaction conditions may include a temperature in a range of from ambient temperature to 500° C. and a pressure of from atmospheric to 600 psi. and at a weight hourly space velocity of 0.25 to 20 $hr^{-1}$.

Optionally in any embodiment, the concentration of the epoxide reagent in the reaction zone is equal to or up to 10% higher than the stoichiometric value for a carbonylation reaction.

Optionally in any embodiment, the reaction zone may receive a Lewis base additive selected from the group consisting of a modified THF; 2,6-lutidine; imidazole, 1-methylimidazole 4-dimethylaminopyridine, trihexylamine and triphenylphosphine.

Optionally in any embodiment, the heterogenous catalyst may comprise an anionic metal carbonyl species having a general formula of $[Q_dM'_e(CO)_w]^{y-}$, where Q is an optional ligand, M' is a metal atom, d is an integer between 0 and 8 inclusive, e is an integer between 1 and 6 inclusive, w is the number needed to provide the stable anionic metal carbonyl complex, y is the charge of the anionic metal carbonyl species and the optional ligand is bound to a solid support comprising at least one material selected from the group consisting of silica, alumina, titania, silica/alumina, pyrogenic silica, high purity silica, zirconia, carbon black, activated carbon and zeolite.

Optionally in any embodiments, the anionic metal carbonyl complex may comprise at least one of $[Co(CO)_4]-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, $[Mn(CO)_5]^-$, and $[Co(CO)_4]^-$.

Optionally in any embodiments, the heterogenous catalyst may comprise a solid support, a cationic Lewis acid functional group and a metal carbonyl compound comprising at least one of anionic metal carbonyl compound or a neutral metal carbonyl compound.

Optionally in any embodiment, the Lewis acid functional group may comprise at least one Lewis acidic metal complex selected from the group consisting of Zn(II), Cu(II), Mn(II), Co(II), Ru(II), Fe(II), Co(II), Rh(II), Ni(II), Pd(II), Mg(II), Al(III), Cr(III), Fe(III), Co(III), Ti(III) In(III), Ga(III), Mn(III), Ti(IV) and Cr(IV).

Optionally in any embodiment, the solid support may comprise one or more zeolites having a faujasite structure, a mordenite structure, a ZSM-5 (MFI) structure, a hexagonal pore arrangement of MCM-41, a cubic pore arrangement of MCM-48, and a lamellar pore arrangement of MCM-50.

More specifically, preferred embodiments of a process for producing a beta-lactone product from a carbon monoxide reagent and an epoxide reagent may be carried out by passing the epoxide reagent to a reaction zone; passing the carbon monoxide reagent to the reaction zone; contacting the epoxide reagent and the carbon monoxide reagent with a heterogenous catalyst at reaction conditions in the reaction zone to produce the beta-lactone product, the heterogenous catalyst may comprise a solid support, a cationic Lewis acid functional group and a metal carbonyl compound. The metal carbonyl compound may comprise at least one of anionic metal carbonyl compound or a neutral metal carbonyl compound. The process may further by carried out by removing the beta-lactone product from the reaction zone.

Another preferred embodiment of a carbonylation process may comprise contacting at least one of epoxide reagent with a carbon monoxide reagent in the presence of a heterogeneous catalyst composition. The heterogeneous catalyst may be obtained by a method. The method may be carried out by impregnating a solid support with a solution comprising a Lewis acid functional group and a metal carbonyl compound in a non-oxygenated hydrocarbon solvent to form the impregnated solid support; and calcining the impregnated solid support to form the catalyst composition. The substantial exclusion of water until at least after step (a) may be completed.

Optionally in any embodiment, the solid support may comprise a crystalline structure by mixing with the crystalline structure followed by drying and calcination to form the heterogenous catalyst.

Optionally in any embodiment, a first metal complex may be mixed with the crystalline structure followed by drying and calcining to produce an impregnated solid support. The impregnated solid support may be mixed with an additional metal complex followed by an additional drying and calcining to form the heterogenous catalyst.

Optionally in any embodiment, the non-oxygenated hydrocarbon solvent may be selected from the group consisting of $C_5$-$C_{12}$ aliphatic hydrocarbons, $C_6$-$C_{12}$ aromatic hydrocarbons, $C_1$-$C_{10}$ halogenated aliphatic hydrocarbons, $C_6$-$C_{10}$ halogenated aromatic hydrocarbons, and mixtures thereof.

Optionally in any embodiment, water may be substantially excluded until after the second step is completed.

Preferred embodiment of a solid carbonylation catalyst useful for producing beta-lactone from reactants may include at least one of epoxide reagent, a carbon monoxide reagent, and mixtures thereof in a carbonylation process. The solid carbonylation catalyst may comprise a solid component comprising a catalytically effective amount of cationic Lewis acid functional group and anionic metal carbonyl compound associated with a solid support. The cationic Lewis acid functional group may be anchored or covalently bonded to the solid support.

Optionally in any embodiment, the carbonylation process may be in a vapor phase or in a liquid phase, for example.

Optionally in any embodiment, the catalyst may comprise from about 0.1 weight percent to about 10 weight percent, preferably about 0.1 weight percent to about 2 weight percent of cationic Lewis acid functional group and anionic metal carbonyl compound.

While this disclosure is susceptible to various modifications and alternative forms, specific exemplary embodiments thereof have been shown by way of example and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

DETAILED DESCRIPTION OF EMBODIMENTS

Definitions

The terms bio-content and bio-based content mean biogenic carbon also known as bio-mass derived carbon, carbon waste streams, and carbon from municipal solid waste. In some variations, bio-content (also referred to as "bio-based content") can be determined based on the following:

Bio-content or Bio-based content=[Bio (Organic) Carbon]/[Total (Organic) Carbon] 100%, as determined by ASTM D6866 (Standard Test Methods for Determining the Bio-based (biogenic) Content of Solid, Liquid, and Gaseous Samples Using Radiocarbon Analysis).

The ASTM D6866 method allows the determination of the bio-based content of materials using radiocarbon analysis by accelerator mass spectrometry, liquid scintillation counting, and isotope mass spectrometry. When nitrogen in the atmosphere is struck by an ultraviolet light produced neutron, it loses a proton and forms carbon that has a molecular weight of 14, which is radioactive. This 14C is immediately oxidized into carbon dioxide, and represents a small, but measurable fraction of atmospheric carbon. Atmospheric carbon dioxide is cycled by green plants to make organic molecules during photosynthesis. The cycle is completed when the green plants or other forms of life metabolize the organic molecules producing carbon dioxide which is then able to return back to the atmosphere. Virtually all forms of life on Earth depend on this green plant production of organic molecules to produce the chemical energy that facilitates growth and reproduction. Therefore, the 14C that exists in the atmosphere becomes part of all life forms and their biological products. These renewably based organic molecules that biodegrade to carbon dioxide do not contribute to global warming because no net increase of carbon is emitted to the atmosphere. In contrast, fossil fuel-based carbon does not have the signature radiocarbon ratio of atmospheric carbon dioxide. See WO 2009/155086, incorporated herein by reference.

The application of ASTM D6866 to derive a "bio-based content" is built on the same concepts as radiocarbon dating, but without use of the age equations. The analysis is performed by deriving a ratio of the amount of radiocarbon (14C) in an unknown sample to that of a modern reference standard. The ratio is reported as a percentage, with the units "pMC" (percent modern carbon). If the material being analyzed is a mixture of present day radiocarbon and fossil carbon (containing no radiocarbon), then the pMC value obtained correlates directly to the amount of bio-based material present in the sample. The modern reference standard used in radiocarbon dating is a NIST (National Institute of Standards and Technology) standard with a known radiocarbon content equivalent approximately to the year AD 1950. The year AD 1950 was chosen because it represented a time prior to thermonuclear weapons testing which introduced large amounts of excess radiocarbon into the atmosphere with each explosion (termed "bomb carbon"). The AD 1950 reference represents 100 pMC. "Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. The distribution of bomb carbon has gradually decreased over time, with today's value being near 107.5 pMC. As a result, a fresh biomass material, such as corn, could result in a radiocarbon signature near 107.5 pMC.

Petroleum-based carbon does not have the signature radiocarbon ratio of atmospheric carbon dioxide. Research has noted that fossil fuels and petrochemicals have less than about 1 pMC, and typically less than about 0.1 pMC, for example, less than about 0.03 pMC. However, compounds derived entirely from renewable resources have at least about 95 percent modern carbon (pMC), they may have at least about 99 pMC, including about 100 pMC.

Combining fossil carbon with present day carbon into a material will result in a dilution of the present day pMC content. By presuming that 107.5 pMC represents present day bio-based materials and 0 pMC represents petroleum derivatives, the measured pMC value for that material will reflect the proportions of the two component types. A material derived 100% from present day biomass would give a radiocarbon signature near 107.5 pMC. If that material were diluted with 50% petroleum derivatives, it would give a radiocarbon signature near 54 pMC.

A bio-based content result is derived by assigning 100% equal to 107.5 pMC and 0% equal to 0 pMC. In this regard, a sample measuring 99 pMC will give an equivalent bio-based content result of 93%.

Assessment of the materials described herein according to the present embodiments is performed in accordance with ASTM D6866 revision 12 (i.e. ASTM D6866-12), the entirety of which is herein incorporated by reference. In some embodiments, the assessments are performed according to the procedures of Method B of ASTM-D6866-12. The mean values encompass an absolute range of 6% (plus and minus 3% on either side of the bio-based content value) to account for variations in end-component radiocarbon signatures. It is presumed that all materials are present day or fossil in origin and that the desired result is the amount of bio-based carbon "present" in the material, not the amount of bio-material "used" in the manufacturing process.

Other techniques for assessing the bio-based content of materials are described in U.S. Pat. Nos. 3,885,155, 4,427,884, 4,973,841, 5,438,194, and 5,661,299, and WO 2009/155086, each of which is incorporated herein by reference.

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain at least one units of unsaturation, but which is not aromatic. Unless otherwise specified, aliphatic groups contain 1-30 carbon atoms. In some aspects, aliphatic groups contain 1-12 carbon atoms. In some aspects, aliphatic groups contain 1-8 carbon atoms. In some aspects, aliphatic groups contain 1-6 carbon atoms. In some aspects, aliphatic groups contain 1-5 carbon atoms, in some aspects, aliphatic groups contain 1-4 carbon atoms, in yet other aspects aliphatic groups contain 1-3 carbon atoms, and in yet other aspects, aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein at least one carbon atoms are independently replaced by at least one atoms selected from the group consisting of oxygen, sulfur, nitrogen, phosphorus, or boron. In some aspects, one or two carbon atoms are independently replaced by at least one of oxygen, sulfur, nitrogen, or phosphorus. Heteroaliphatic groups may be substituted or unsubstituted, branched or unbranched, cyclic or acyclic, and include "heterocycle," "heterocyclyl," "heterocycloaliphatic," or "heterocyclic" groups.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate.

The term "polymer", as used herein, refers to a molecule of high relative molecular mass, the structure of which comprises the multiple repetitions of units derived, actually or conceptually, from molecules of low relative molecular mass. In some aspects, a polymer is comprised of only one monomer species. In some aspects, a polymer is a copolymer, terpolymer, heteropolymer, block copolymer, or tapered heteropolymer of at least one epoxides.

The term "unsaturated", as used herein, means that a moiety has at least one double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cyclohepte-nyl, cyclooctyl, cyclooctenyl, and cyclooctadienyl. In some aspects, the cycloalkyl has 3-6 carbons. Representative carbocyles include cyclopropane, cyclobutane, cyclopentane, cyclohexane, bicyclo[2,2,1]heptane, norbornene, phenyl, cyclohexene, naphthalene, and spiro[4.5]decane. The terms "cycloaliphatic", "carbocycle" or "carbocyclic" also include aliphatic rings that are fused to at least one aromatic or nonaromatic rings, such as decahydronaphthyl or tetrahydronaphthyl, where the radical or point of attachment is on the aliphatic ring. In some aspects, a carbocyclic group is bicyclic. In some aspects, a carbocyclic group is tricyclic. In some aspects, a carbocyclic group is polycyclic.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In some aspects, alkyl groups contain 1-8 carbon atoms. In some aspects, alkyl groups contain 1-6 carbon atoms. In some aspects, alkyl groups contain 1-5 carbon atoms, in some aspects, alkyl groups contain 1-4 carbon atoms, in yet other aspects, alkyl groups contain 1-3 carbon atoms, and in yet other aspects alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In some aspects, "aryl" refers to an aromatic ring system which includes, but is not limited to, phenyl, naphthyl, anthracyl and the like, which may bear at least one substituents. Also included within the scope of the term "aryl", as it is used herein, is a group in which an aromatic ring is fused to at least one additional rings, such as benzofuranyl, indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to at least one aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3- b]-1,4-oxazin-3(4H)-one. A heteroaryl group may be monocyclic or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7- to 14-membered bicyclic heterocyclic moiety that is either saturated or partially unsaturated, and having, in addition to carbon atoms, at least one, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to at least one aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds may contain "optionally substituted" moieties. In general, the term "substituted", whether preceded by the term "optionally" or not, means that at least one hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned may include those that result in the formation of stable or chemically feasible compounds. The term "stable", as used herein, refers to compounds that are not substantially altered when subjected to conditions to allow for their production, detection, and, in some aspects, their recovery, purification, and use for at least one of the purposes disclosed herein.

In some chemical structures herein, substituents are shown attached to a bond which crosses a bond in a ring of the depicted molecule. This means that at least one of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

As used herein, the term "catalyst" refers to a substance the presence of which increases the rate of a chemical reaction, while not being consumed or undergoing a permanent chemical change itself.

Renewable sources means a source of carbon and/or hydrogen obtained from biological life forms that can replenish itself in less than one hundred years.

Renewable carbon means carbon obtained from biological life forms that can replenish itself in less than one hundred years.

Recycled sources mean carbon and/or hydrogen recovered from a previous use in a manufactured article.

Recycled carbon means carbon recovered from a previous use in a manufactured article.

As used herein, the term "about" preceding at least one numerical values means the numerical value ±5%. It should be understood that reference to "about" a value or parameter herein includes (and describes) aspects that are directed to that value or parameter per se. For example, description referring to "about x" includes description of "x" per se.

Further, it should be understood that reference to "between" two values or parameters herein includes (and describes) aspects that include those two values or parameters per se. For example, description referring to "between x and y" includes description of "x" and "y" per se.

The mass fractions disclosed herein can be converted to wt % by multiplying by 100.

EXEMPLARY EMBODIMENTS

In preferred embodiments of the present invention, the processes include a step for reacting the contents of a feed stream comprising an epoxide reagent and a carbon monoxide reagent with a heterogenous catalyst in a reaction zone to produce a product stream comprising a beta-lactone product. Preferably, the beta-lactone product may be removed from the reaction zone in a liquid phase or a gas phase. In preferred embodiments, the heterogenous catalyst is in a solid phase. Advantageously, the processes of the present invention do not require a membrane, filter, or sieve to remove the heterogenous catalyst from the beta-lactone product.

In certain preferred embodiments of the present invention, the processes comprise the steps: passing a feed stream comprising an epoxide reagent and a carbon monoxide reagent to a reaction zone; contacting the epoxide reagent and the carbon monoxide reagent with a heterogenous catalyst to produce a beta-lactone product in the reaction zone; and removing the beta-lactone product from the reaction zone. Preferably, the processes of the present invention do not require the use of solvent to dissolve reagents or products. Therefore, certain embodiments of the processes do not require a distillation step to separate the beta-lactone product from a solvent.

In certain other preferred embodiments, the processes comprise the steps: passing a feed stream comprising an epoxide reagent and a carbon monoxide reagent to a reaction zone; contacting the epoxide reagent and the carbon monoxide reagent with a heterogenous catalyst to produce a beta-lactone intermediate in the reaction zone; reacting the beta-lactone intermediate with a derivative reagent in the reaction zone to produce a beta-lactone derivative; and removing the beta-lactone derivative from the reaction zone. A derivative reagent may be chosen from a list including a carbon monoxide reagent, beta-lactone reagent, an ammonia reagent, an alcohol reagent. Preferably, the beta-lactone intermediate remains in the reactor and is reacted with the derivative reagent. Advantageously, the processes of the present invention do not require unnecessary steps for separation or isolation of intermediates.

Embodiments of the present invention configured for producing a beta-lactone derivative may include the insertion of a heteroatom such as by nucleophilic addition. Typical heteroatoms are nitrogen, oxygen, sulfur, phosphorus, chlorine, bromine, and iodine and includes any oxidized form of nitrogen or sulfur, and any quaternized form of a basic nitrogen. In certain preferred embodiments, the insertion of the heteroatom opens the beta-lactone ring and adds a hydroxyl group, hydroxyalkyl group, amine group, amide group, ester group, carbonyl group, carbonate group, carboxylic acid group, aldehyde group, keto group, ether group, and/or urethane group to name a few.

In still other preferred embodiments, the processes comprise the steps: passing a feed stream comprising an epoxide reagent and a carbon monoxide reagent to a reaction zone through a feed stream inlet; contacting the epoxide reagent and the carbon monoxide reagent with a heterogenous catalyst to produce a beta-lactone intermediate in the reactor; polymerizing the beta-lactone intermediate in the reactor to produce a polylactone product; removing the polylactone product from the reactor through a product stream outlet.

In certain embodiments, the processes of the present invention are performed with a reactor configured for a continuous operation and wherein the epoxide reagent and carbon monoxide reagent are continuously fed to a reaction zone of the reactor. In some embodiments, the reactor is mixed. In other embodiments, there is no mixing in the reactor. In some embodiments, the epoxide reagent and/or carbon monoxide reagent may be fed to the reactor at ambient temperature and pressure and then heated or pressurized to reaction conditions once in the reactor. In other embodiments, the epoxide reagent and/or carbon monoxide reagent may be fed to the reactor above ambient temperature and pressure. The reactor itself may be any reactor conducive to continuous operation, including but not limited to a fixed bed reactor, moving bed reactor, fluidized bed reactor, trickle bed reactor, catalytic distillation reactor, continuously stirred tank reactor, or a tubular reactor. In some embodiments, the reactor is an adiabatic reactor, and/or an isothermal reactor. In some embodiments, the reactor pressure is constant. In some embodiments, the reactor pressure varies as the reaction progresses. In some embodiments, the reactor temperature varies as the reaction progress. In some embodiments, the reaction is performed in a batch operation. One of ordinary skill in the art will recognize the temperatures, pressures, catalyst ratios, concentrations of reactants, and flow rates can all be optimized or varied to achieve a given reaction outcome.

In certain preferred embodiments, the processes of the present invention may include an epoxide reagent and carbon monoxide reagent introduced to a reactor in an amount sufficient for carbonylation under superatmospheric pressure. In certain embodiments, the epoxide reagent and/or carbon monoxide reagent is provided at a pressure in the range from about 50 psi (350 kPa) to about 5000 psi (35 MPa). In certain embodiments, the epoxide reagent and/or carbon monoxide reagent is more preferably provided at a pressure from about 200 psi (1.4 MPa) to about 600 psi (4.1 MPa).

In some embodiments, the processes of the present invention may introduce the epoxide reagent and/or carbon monoxide reagent at a weight hourly space velocity of 0.1 to 20 $hr^{-1}$, more typically 0.25 to 10 $hr^{-1}$, and preferably, 0.5 to 5 $hr^{-1}$. In some embodiments, the flow rate from the epoxide reagent and/or carbon monoxide reagent is set to about the stoichiometric value for a carbonylation reaction, to about 0.1% higher than the stoichiometric value, to about 1% higher than the stoichiometric value, to about 5% higher than the stoichiometric value, to about 10% higher than the stoichiometric value, to about 15% higher than the stoichiometric value, or to about 20% higher than the stoichiometric value. In certain preferred embodiments, the flow rate from the epoxide reagent is set to at least 0.1% higher than the stoichiometric value for a carbonylation reaction.

In some embodiments, the feed stream includes a Lewis base additive. In some embodiments, such Lewis base additives can stabilize or reduce deactivation of the heterogenous catalyst. In some embodiments, the Lewis base additive is a modified THF; 2,6-lutidine; imidazole, 1-methylimidazole 4-dimethylaminopyridine, trihexylamine and triphenylphosphine.

Within the reactor, the epoxide reagent and carbon monoxide reagent contact the heterogenous catalyst to produce at least one beta-lactone and/or beta-lactone derivative. The beta-lactones and beta-lactone derivatives that can be produced from epoxide reagents and/or carbon monoxide reagents may have a bio-content of at least 10% and preferably at least at least 30%, at least 50%, at least 70%, at least 90%, at least 95%, at least 99%, or 100%. Table 1 illustrated below includes Column A directed to a non-exhaustive list of epoxides which may undergo carbonylation to produce beta-lactone according to the processes of the present invention and Column B directed to a non-exhaustive list of beta-lactones which may be produced according to the present invention.

| Column A | Column B |
|---|---|
|  |  |

-continued
| Column A | Column B |
|---|---|
| 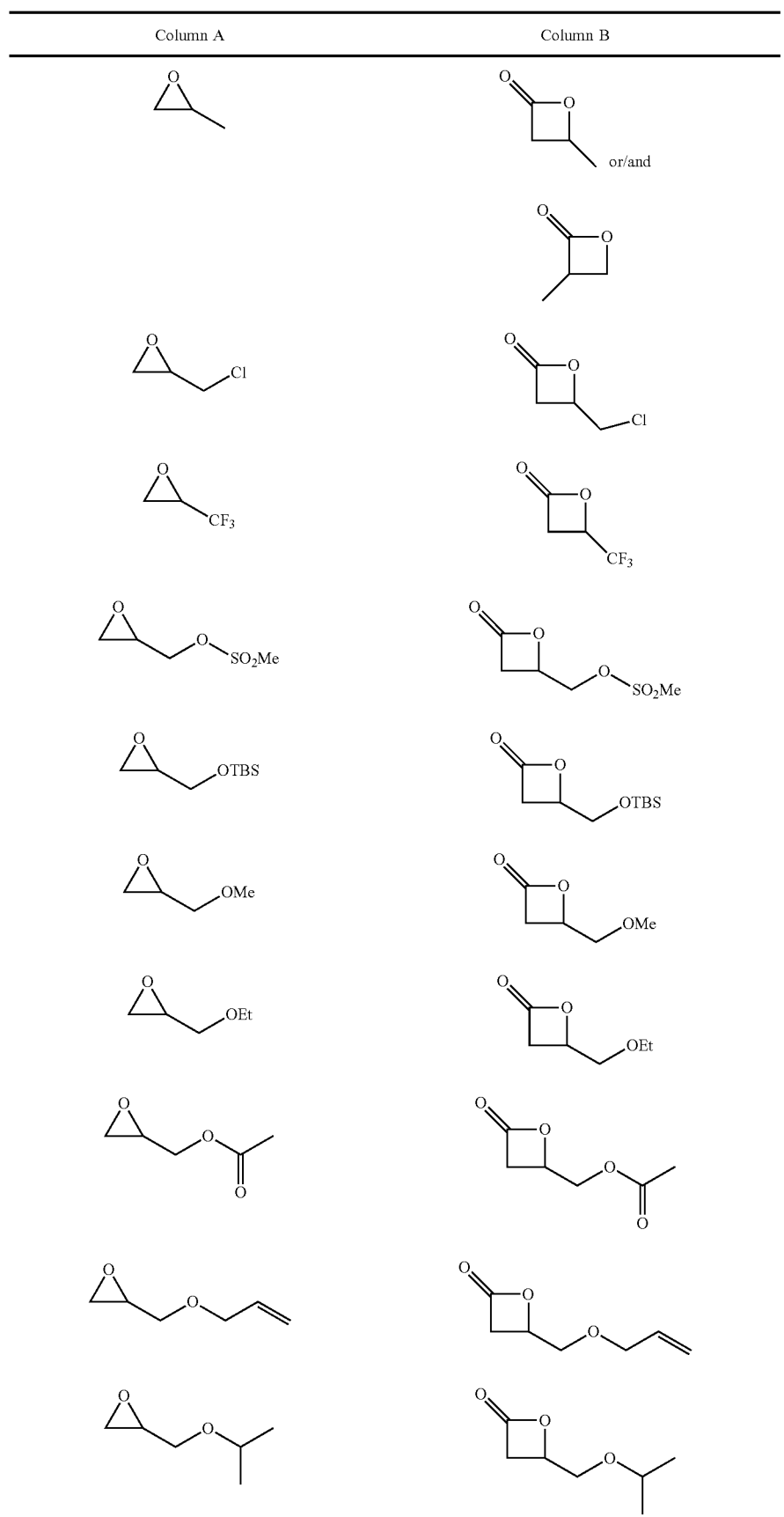 | |

-continued
| Column A | Column B |
|---|---|
| 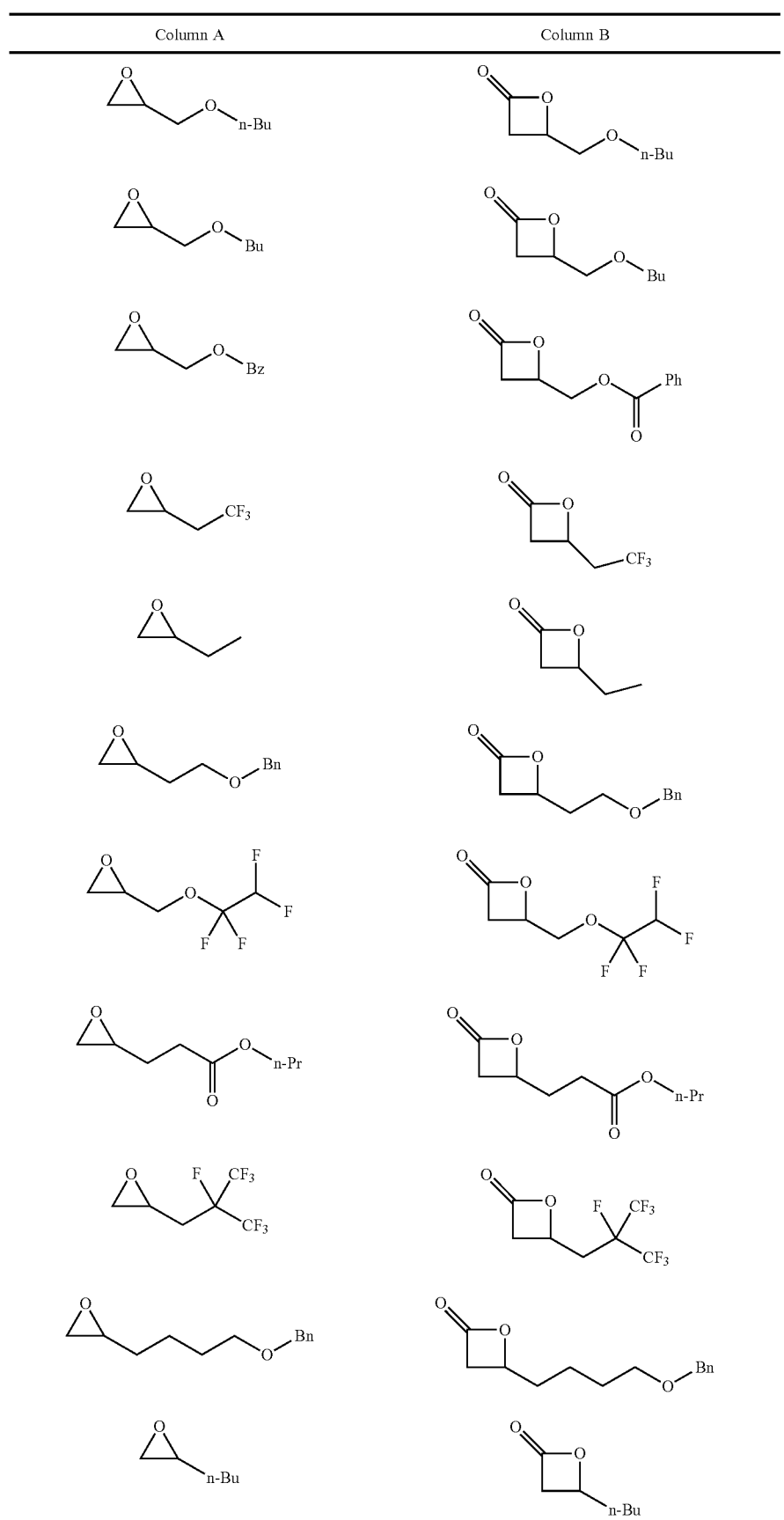 | |

-continued
| Column A | Column B |
| --- | --- |
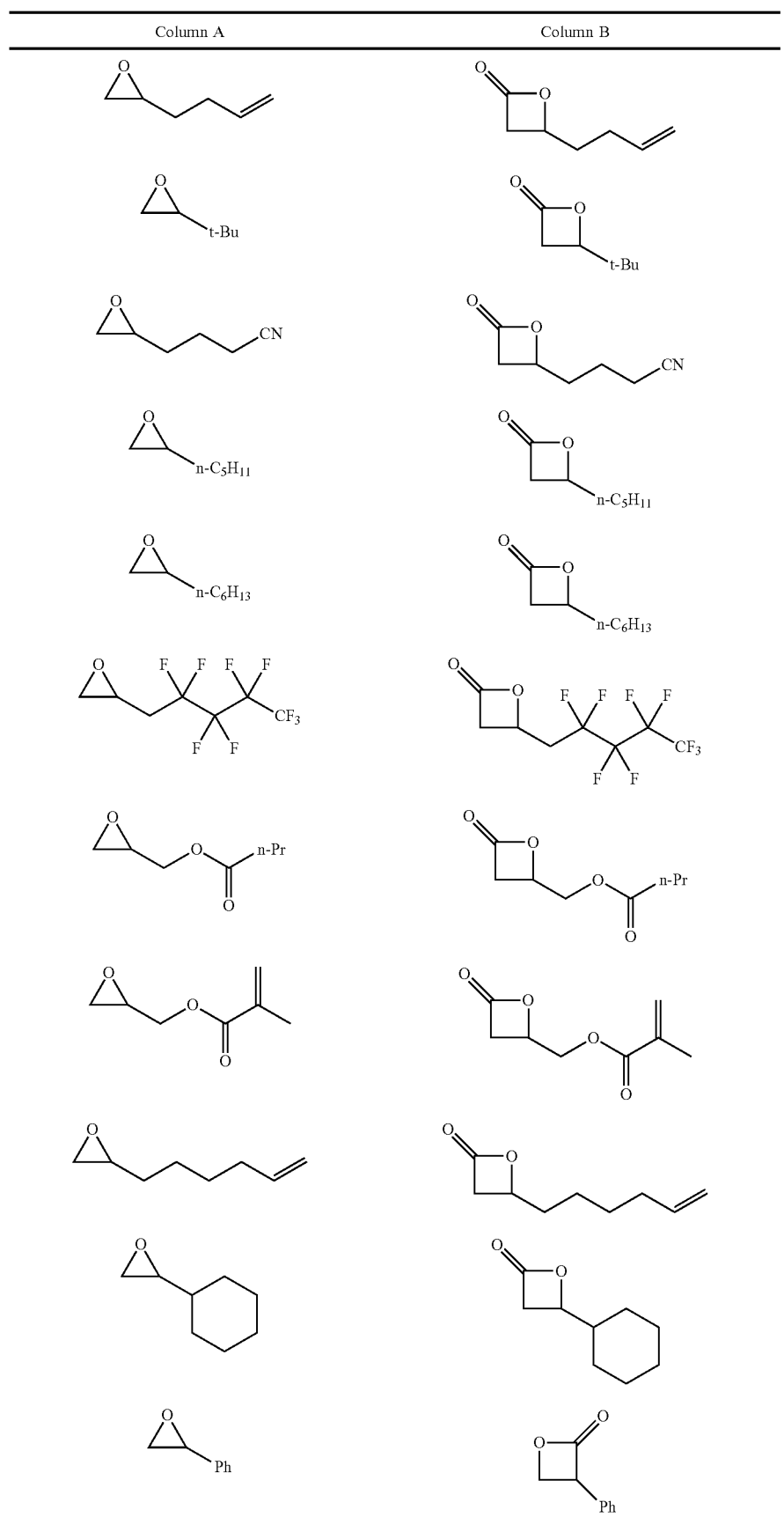

-continued
| Column A | Column B |
|---|---|
| 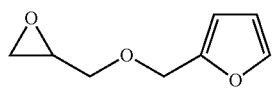 | 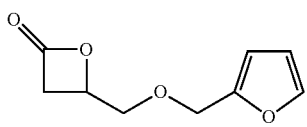 [SMILES: O=C1CC(COCc2ccco2)O1] |
| 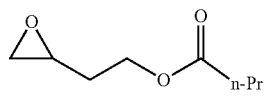 | 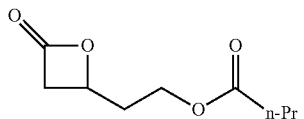 |
| 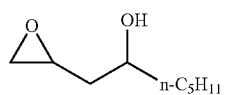 | 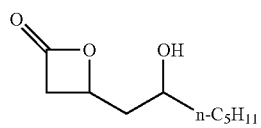 |
| 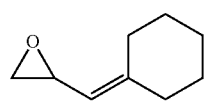 | 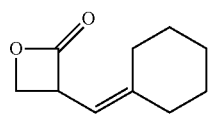 |
|  | 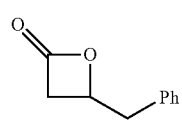 |
| 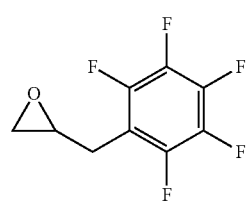 [SMILES: Fc1c(F)c(F)c(CC2CO2)c(F)c1F] | 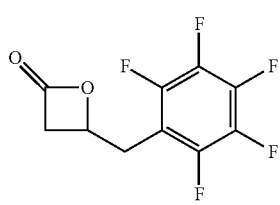 [SMILES: O=C1CC(Cc2c(F)c(F)c(F)c(F)c2F)O1] |
| 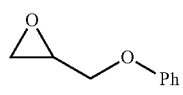 | 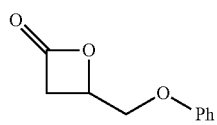 [SMILES: O=C1CC(COc2ccccc2)O1] |
| 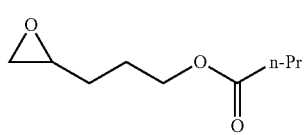 | 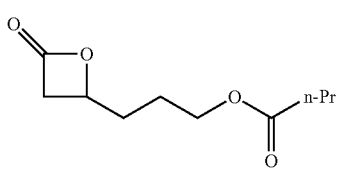 |
| 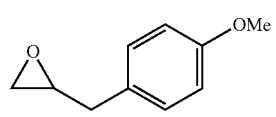 [SMILES: COc1ccc(CC2CO2)cc1] | 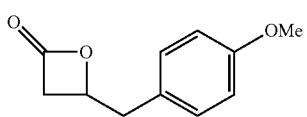 [SMILES: COc1ccc(CC2CC(=O)O2)cc1] |
| 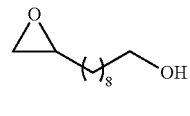 | 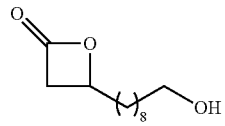 |
| 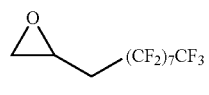 | 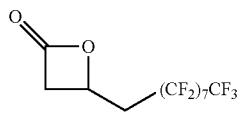 |

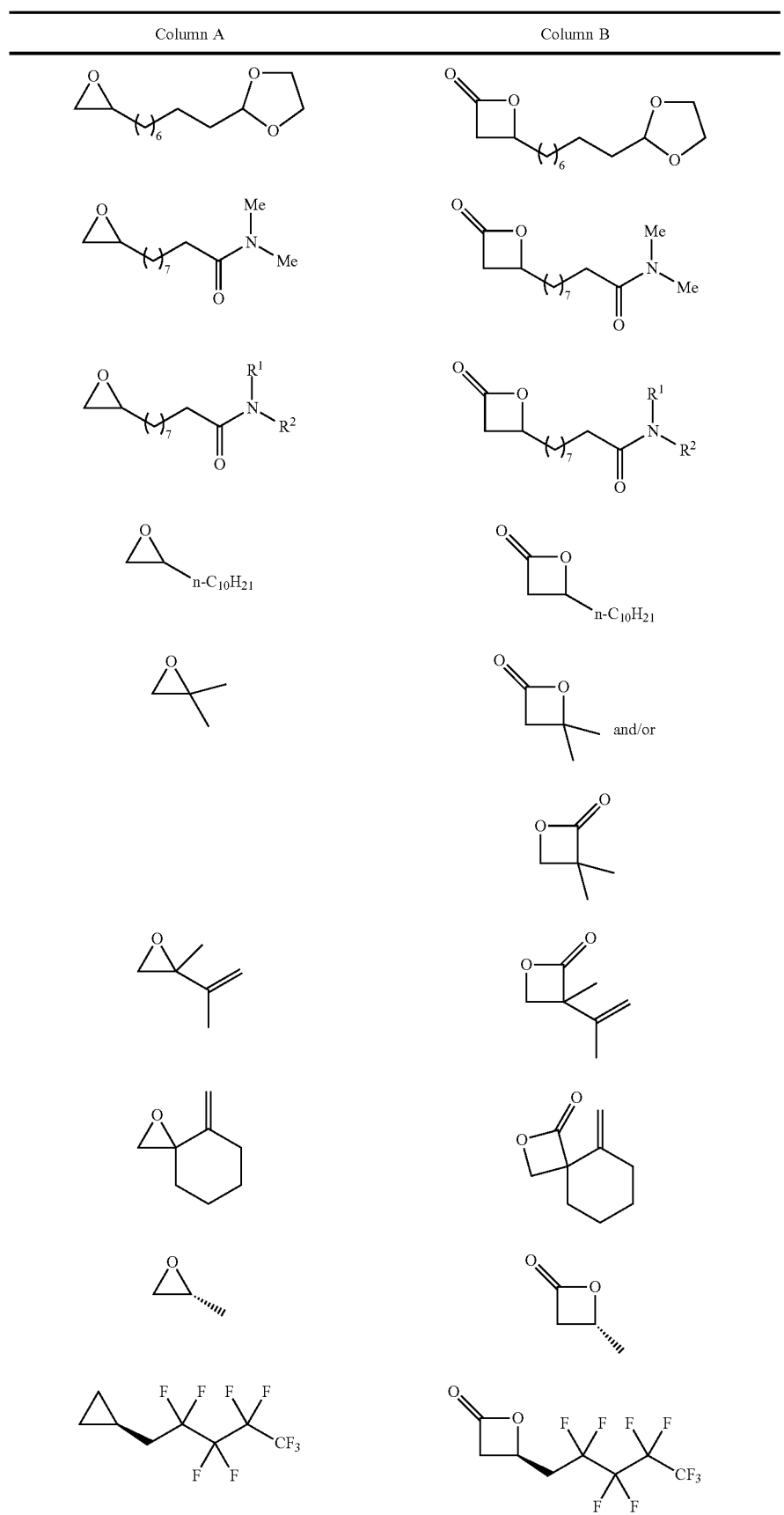

-continued
| Column A | Column B |
|---|---|
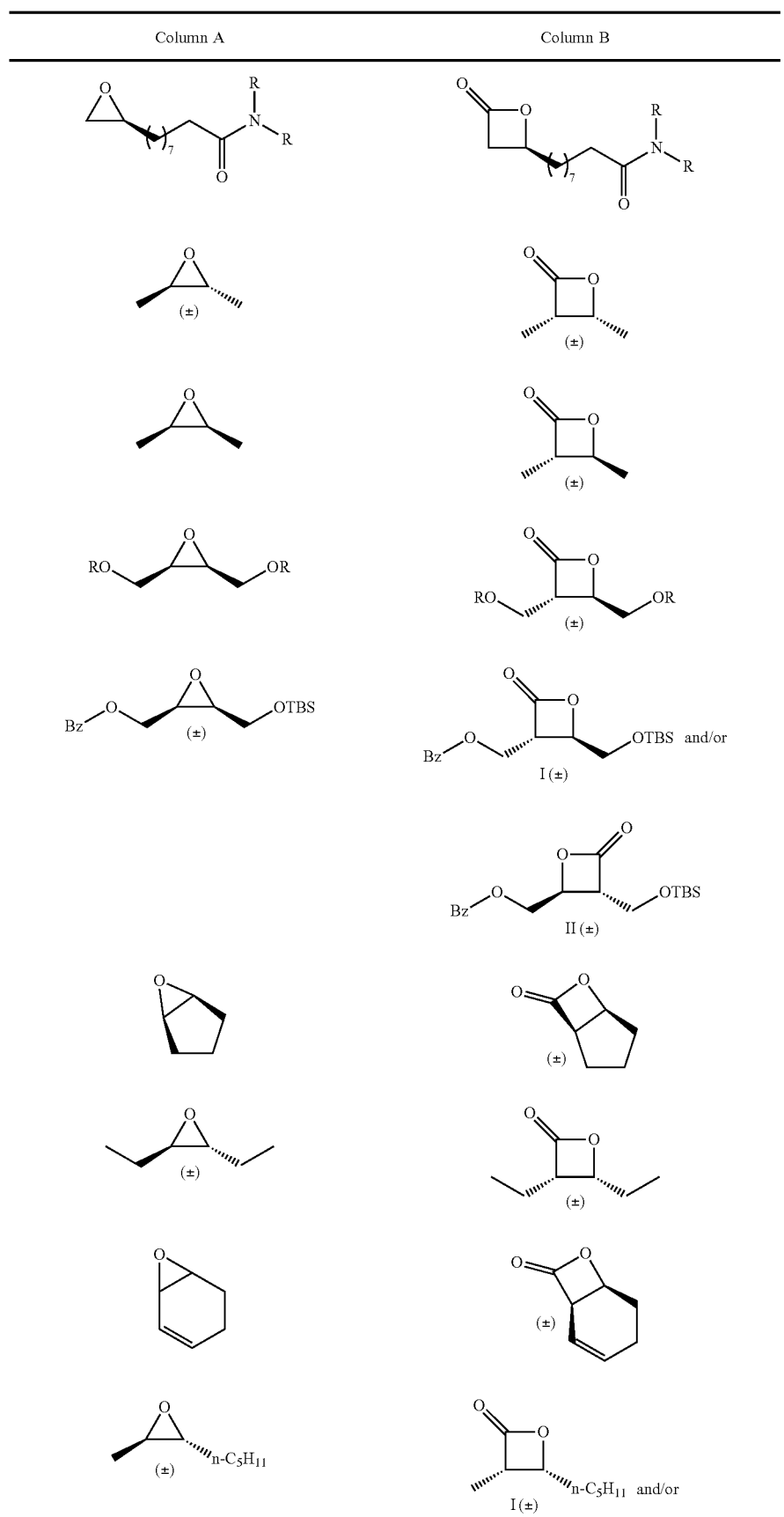

-continued
| Column A | Column B |
|---|---|
| 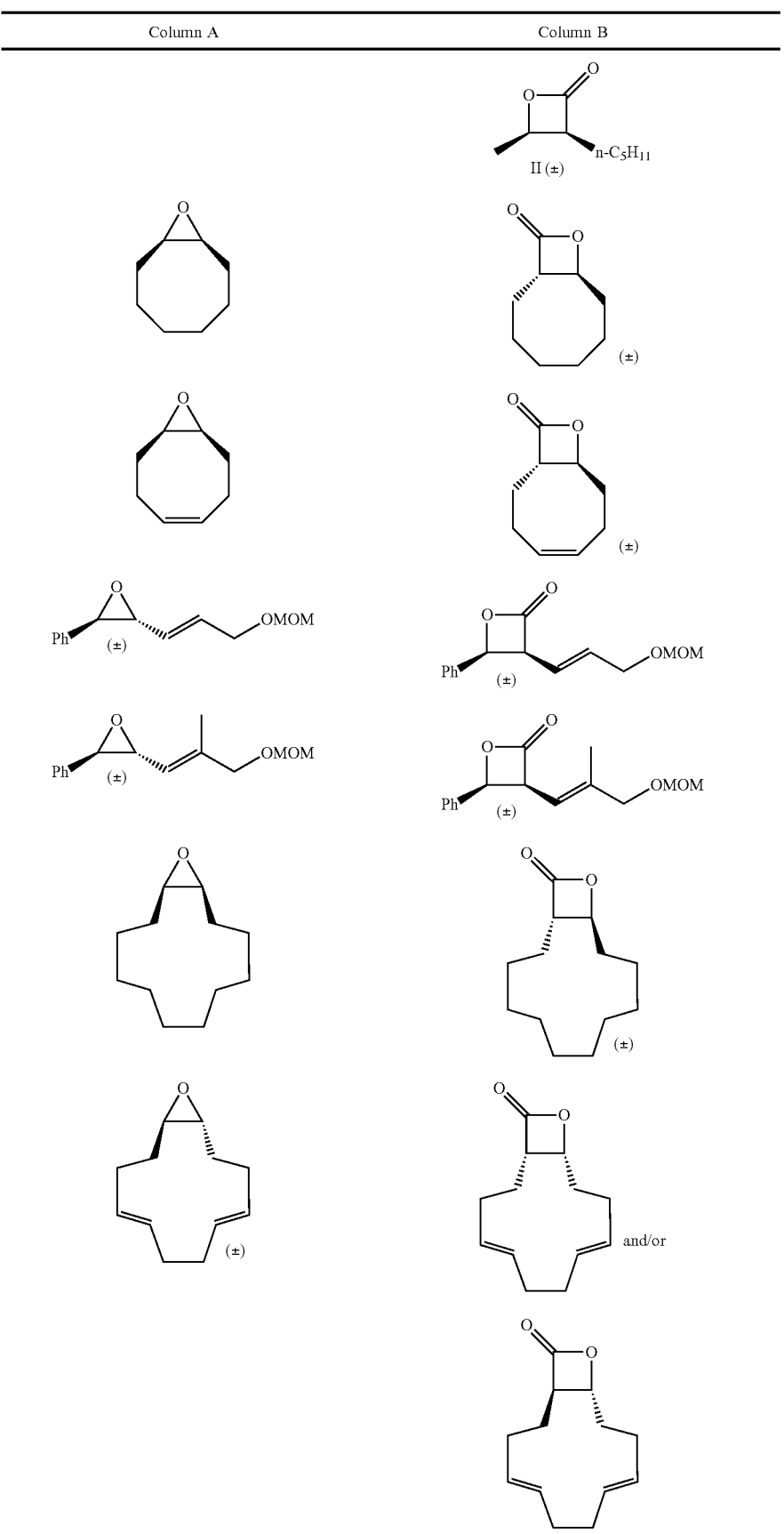 | |

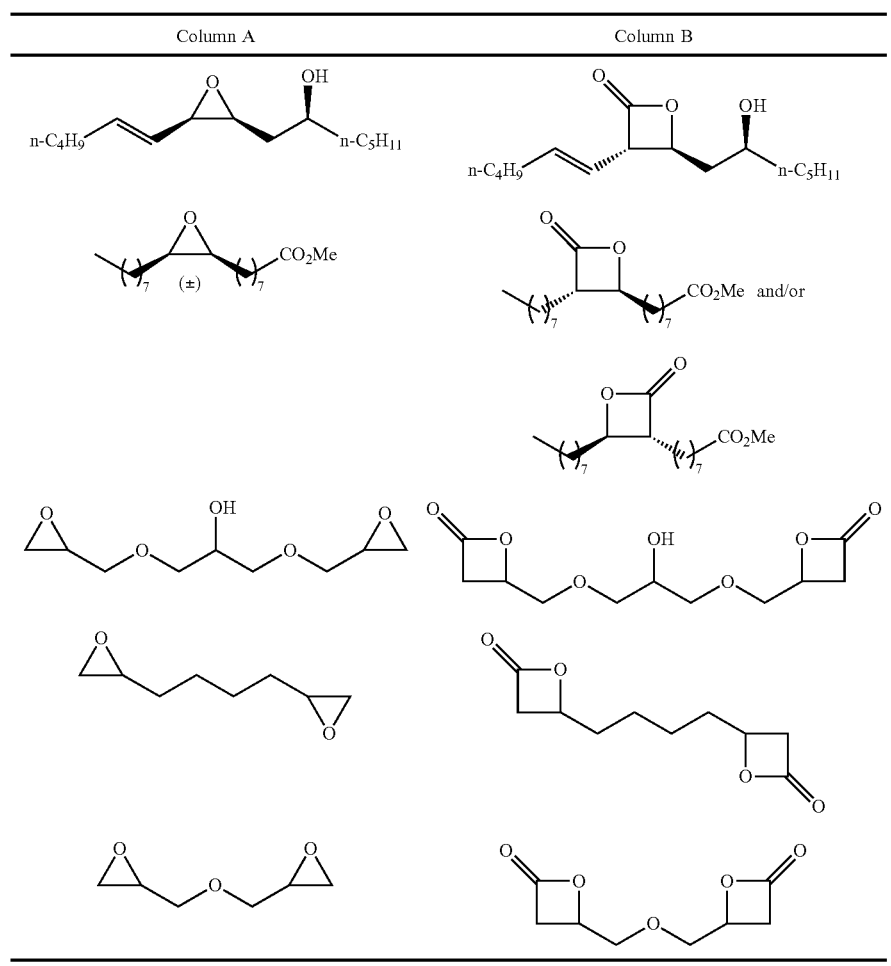

In certain preferred embodiments, the heterogenous catalyst includes a single metal carbonyl compound, but in certain other preferred embodiments, mixtures of two or more metal carbonyl compounds are provided. Thus, when a provided metal carbonyl compound "comprises", e.g., a neutral metal carbonyl compound, it is understood that the provided metal carbonyl compound can be a single metal carbonyl compound, or a metal carbonyl compound in combination with one or more metal carbonyl compounds. Preferably, the provided metal carbonyl compound is capable of ring-opening an epoxide and facilitating the insertion of carbon monoxide into the resulting metal carbon bond. Metal carbonyl compounds with this reactivity are well known in the art and are used for laboratory experimentation as well as in industrial processes such as hydroformylation.

In certain embodiments, metal carbonyl compounds include those described in U.S. Pat. No. 6,852,865. In other embodiments, the metal carbonyls may be those disclosed in U.S. patent application Ser. Nos. 10/820,958; and 10/586,826. In yet other embodiments, the metal carbonyls may be those disclosed in U.S. Pat. Nos. 5,310,948; 7,420,064; and 5,359,081. Additional catalysts for the carbonylation of epoxides are discussed in a review in Chem. Commun., 2007, 657-674. The entirety of each of the preceding references is incorporated herein by reference.

In some embodiments, a provided metal carbonyl compound comprises an anionic metal carbonyl moiety. In other embodiments, a provided metal carbonyl compound comprises a neutral metal carbonyl compound. In some embodiments, a provided metal carbonyl compound comprises a metal carbonyl hydride or a hydrido metal carbonyl compound. In some embodiments, a provided metal carbonyl compound acts as a pre-catalyst which reacts in situ with one or more reaction components to provide an active species different from the compound initially provided. Such pre-catalysts are specifically encompassed as it is recognized that the active species in a given reaction may not be known with certainty; thus the identification of such a reactive species in situ does not itself depart from the spirit or teachings of the present disclosure.

In some embodiments, the metal carbonyl compound comprises an anionic metal carbonyl species. In some embodiments, such anionic metal carbonyl species have the general formula $[Q_d M'_e(CO)_w]^{y-}$, where Q is any ligand and need not be present, M' is a metal atom, d is an integer between 0 and 8 inclusive, e is an integer between 1 and 6 inclusive, w is a number such as to provide the stable anionic metal carbonyl complex, and y is the charge of the anionic metal carbonyl species. In some embodiments, the anionic metal carbonyl has the general formula $[QM'(CO)_w]^{y-}$, where Q is any ligand and need not be present, M' is a metal atom, w is a number such as to provide the stable anionic metal carbonyl, and y is the charge of the anionic metal carbonyl.

In some embodiments, the anionic metal carbonyl species include monoanionic carbonyl complexes of metals from groups 5, 7 or 9 of the periodic table or dianionic carbonyl complexes of metals from groups 4 or 8 of the periodic table. In some embodiments, the anionic metal carbonyl compound contains cobalt or manganese. In some embodiments, the anionic metal carbonyl compound contains rhodium. Suitable anionic metal carbonyl compounds include, but are not limited to: $[Co(CO)_4]^-$, $[Ti(CO)_6]^{2-}$, $[V(CO)_6]^-$ $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, and $[Mn(CO)_5]^-$. In some embodiments, the anionic metal carbonyl comprises $[Co(CO)_4]^-$. In some embodiments, a mixture of two or more anionic metal carbonyl complexes may be present in the heterogenous catalysts used in the methods.

The term "such as to provide a stable anionic metal carbonyl" for $[Q_dM'_e(CO)_{w'}]^{y-}$ is used herein to mean that $[Q_dM'_e(CO)_{w'}]^{y-}$ is a species characterizable by analytical means, e.g., NMR, IR, X-ray crystallography, Raman spectroscopy and/or electron spin resonance (EPR) and isolable in catalyst form in the presence of a suitable cation or a species formed in situ. It is to be understood that metals which can form stable metal carbonyl complexes have known coordinative capacities and propensities to form polynuclear complexes which, together with the number and character of optional ligands Q that may be present and the charge on the complex will determine the number of sites available for carbon monoxide to coordinate and therefore the value of w. Typically, such compounds conform to the "18-electron rule". Such knowledge is within the grasp of one having ordinary skill in the arts pertaining to the synthesis and characterization of metal carbonyl compounds.

In embodiments including an anionic metal carbonyl, one or more cations must also necessarily be present. In some variations, no particular constraints on the identity of such cations. In some embodiments, the cation associated with an anionic metal carbonyl compound comprises a reaction component of another category described herein. For example, in some embodiments, the metal carbonyl anion is associated with a cationic Lewis acid. In other embodiments, a cation associated with a provided anionic metal carbonyl compound is a simple metal cation such as those from Groups 1 or 2 of the periodic table (e.g., $Na^+$, $Li^+$, $K^+$, $Mg^{2+}$ and the like). In other embodiments, a cation associated with a provided anionic metal carbonyl compound is a bulky non electrophilic cation such as an 'onium salt' (e.g., $Bu_4N^+$, $PPN^+$, $Ph_4P^+$ $Ph_4As^+$, and the like). In other embodiments, a metal carbonyl anion is associated with a protonated nitrogen compound (e.g., a cation may comprise a compound such as MeTBD-H$^+$, DMAP-H$^+$, DABCO-H$^+$, DBU-H$^+$ and the like). In some embodiments, compounds comprising such protonated nitrogen compounds are provided as the reaction product between an acidic hydrido metal carbonyl compound and a basic nitrogen-containing compound (e.g., a mixture of DBU and $HCo(CO)_4$).

In some embodiments, a catalyst utilized in the methods described herein comprises a neutral metal carbonyl compound. In some embodiments, such neutral metal carbonyl compounds have the general formula $Q_dM'_e(CO)_{w'}$, where Q is any ligand and need not be present, M' is a metal atom, d is an integer between 0 and 8 inclusive, e is an integer between 1 and 6 inclusive, and w' is a number such as to provide the stable neutral metal carbonyl complex. In some embodiments, the neutral metal carbonyl has the general formula $QM'(CO)_{w'}$. In some embodiments, the neutral metal carbonyl has the general formula $M'(CO)_{w'}$. In some embodiments, the neutral metal carbonyl has the general formula $QM'_2(CO)_{w'}$. In some embodiments, the neutral metal carbonyl has the general formula $M'_2(CO)_{w'}$. Suitable neutral metal carbonyl compounds include, but are not limited to: $Ti(CO)_7$; $V_2(CO)_{12}$; $Cr(CO)_6$; $Mo(CO)_6$; $W(CO)_6$ $Mn_2(CO)_{10}$, $Tc_2(CO)_{10}$, and $Re_2(CO)_{10}$ $Fe(CO)_5$, $Ru(CO)_5$ and $Os(CO)_5$ $Ru_3(CO)_{12}$, and $Os_3(CO)_{12}$ $Fe_3(CO)_{12}$ and $Fe_2(CO)_9$ $Co_4(CO)_{12}$, $Rh_4(CO)_{12}$, $Rh_6(CO)_{16}$, and $Ir_4(CO)_{12}$ $Co_2(CO)_8$ $Ni(CO)_4$.

The term "such as to provide a stable neutral metal carbonyl" for $Q_dM'_e(CO)_{w'}$ is used herein to mean that $Q_dM'_e(CO)_{w'}$ is a species characterizable by analytical means, e.g., NMR, IR, X-ray crystallography, Raman spectroscopy and/or electron spin resonance (EPR) and isolable in pure form or a species formed in situ. It is to be understood that metals which can form stable metal carbonyl complexes have known coordinative capacities and propensities to form polynuclear complexes which, together with the number and character of optional ligands Q that may be present will determine the number of sites available for carbon monoxide to coordinate and therefore the value of w'. Typically, the stoichiometry of such compounds conforms to the "18-electron rule". Such knowledge is within the grasp of one having ordinary skill in the arts pertaining to the synthesis and characterization of metal carbonyl compounds.

In some embodiments, no ligands Q are present on the metal carbonyl compound. In other embodiments, one or more ligands Q are present on the metal carbonyl compound. In some embodiments, where Q is present, each occurrence of Q is selected from the group consisting of phosphine ligands, amine ligands, cyclopentadienyl ligands, heterocyclic ligands, nitriles, phenols, and combinations of two or more of these. In some embodiments, one or more of the CO ligands of any of the metal carbonyl compounds described above is replaced with a ligand Q. In some embodiments, Q is a phosphine ligand. In some embodiments, Q is a triaryl phosphine. In some embodiments, Q is trialkyl phosphine. In some embodiments, Q is a phosphite ligand. In some embodiments, Q is an optionally substituted cyclopentadienyl ligand. In some embodiments, Q is cp. In some embodiments, Q is cp*. In some embodiments, Q is an amine or a heterocycle.

In some embodiments, the heterogenous catalyst utilized in the methods described above further includes a Lewis acidic component. In some embodiments, the heterogenous catalyst includes an anionic metal carbonyl complex and a cationic Lewis acidic component. In some embodiments, the metal carbonyl complex includes a carbonyl cobaltate and the Lewis acidic co-catalyst includes a metal-centered cationic Lewis acid. In some embodiments, an included Lewis acid comprises a boron compound.

In some embodiments, where an included Lewis acid comprises a boron compound, the boron compound comprises a trialkyl boron compound or a triaryl boron compound. In some embodiments, an included boron compound comprises one or more boron-halogen bonds. In some embodiments, where an included boron compound comprises one or more boron-halogen bonds, the compound is a dialkyl halo boron compound (e.g., $R_2BX$), a dihalo monoalkyl compound (e.g., $RBX_2$), an aryl halo cboron compound (e.g., $Ar_2BX$ or $ArBX_2$), or a trihalo boron compound (e.g., $BCl_3$ or $BBr_3$), wherein each R is an alkyl group; each X is a halogen; and each Ar is an aromatic group.

In some embodiments, where the included Lewis acid comprises a metal-centered cationic Lewis acid, the Lewis acid is a cationic metal complex. In some embodiments, the cationic metal complex has its charge balanced either in part, or wholly by one or more anionic metal carbonyl moieties. Suitable anionic metal carbonyl compounds include those described above. In some embodiments, there are 1 to 17 such anionic metal carbonyls balancing the charge of the metal complex. In some embodiments, there are 1 to 9 such anionic metal carbonyls balancing the charge of the metal complex. In some embodiments, there are 1 to 5 such anionic metal carbonyls balancing the charge of the metal complex. In some embodiments, there are 1 to 3 such anionic metal carbonyls balancing the charge of the metal complex.

In some embodiments, where the heterogenous catalysts used in the processes described herein include a cationic metal complex, the metal complex has the formula $[(L^c)_v M_b]^{z+}$, where:

$L^c$ is a ligand where, when two or more $L^c$ are present, each may be the same or different;

M is a metal atom where, when two M are present, each may be the same or different;

v is an integer from 1 to 4 inclusive;

b is an integer from 1 to 2 inclusive; and z is an integer greater than 0 that represents the cationic charge on the metal complex.

In some embodiments, provided Lewis acids conform to structure I:

wherein:

is a multidentate ligand;

M is a metal atom coordinated to the multidentate ligand;

a is the charge of the metal atom and ranges from 0 to 2; and

In some embodiments, provided metal complexes conform to structure II:

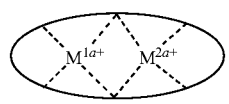
II

Where a is as defined above (each a may be the same or different), and $M^1$ is a first metal atom;

$M^2$ is a second metal atom;

comprises a multidentate ligand system capable of coordinating both metal atoms.

For sake of clarity, and to avoid confusion between the net and total charge of the metal atoms in complexes I and II and other structures herein, the charge ($a^+$) shown on the metal atom in complexes I and II above represents the net charge on the metal atom after it has satisfied any anionic sites of the multidentate ligand. For example, if a metal atom in a complex of formula I were Cr(III), and the ligand were porphyrin (a tetradentate ligand with a charge of −2), then the chromium atom would have a net charge of +1, and a would be 1.

Suitable multidentate ligands include, but are not limited to: porphyrin derivatives 1, salen derivatives 2, dibenzotetramethyltetraaza[14]annulene (tmtaa) derivatives 3, phthalocyaninate derivatives 4, derivatives of the Trost ligand 5, tetraphenylporphyrin derivatives 6, and corrole derivatives 7. In some embodiments, the multidentate ligand is a salen derivative. In other embodiments, the multidentate ligand is a porphyrin derivative. In other embodiments, the multidentate ligand is a tetraphenylporphyrin derivative. In other embodiments, the multidentate ligand is a corrole derivative.

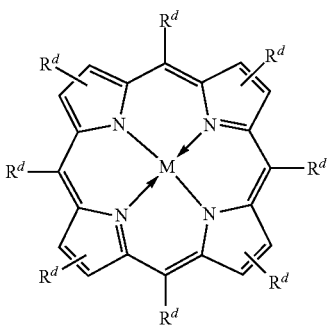
1

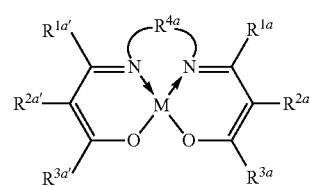
2

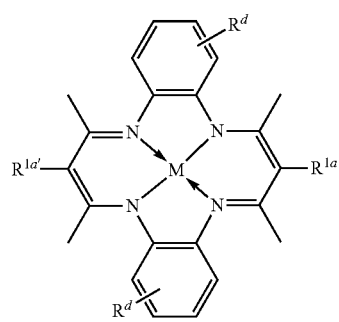
3

4

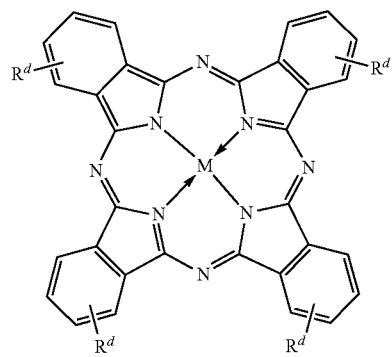

5

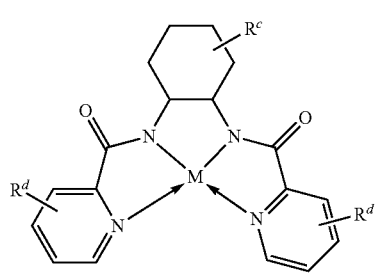

6

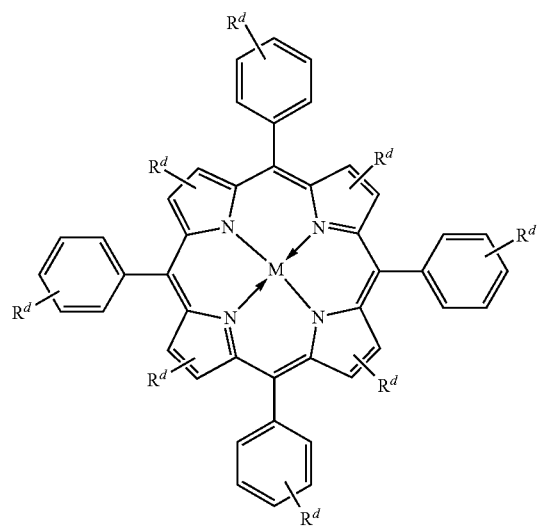

7

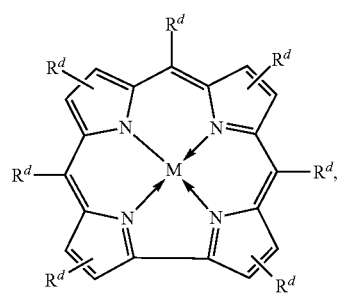

where each of $R^c$, $R^d$, $R^{1a}$, $R^{2a}$, $R^{3a}$, $R^{4a}$, $R^{2a\prime}$, $R^{3a\prime}$, and M, is as defined and described in the classes and subclasses herein.

In some embodiments, Lewis acids provided heterogenous catalysts used in systems and methods described herein comprise metal-porphinato complexes. In some embodiments, the moiety

has the structure:

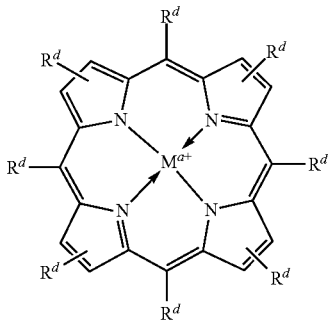

where each of M and a is as defined above and described in the classes and subclasses herein, and $R^d$ at each occurrence is independently hydrogen, halogen, —$OR^4$, —$NR^y{}_2$, —$SR^y$, —CN, —$NO_2$, —$SO_2R^y$, —$SOR^y$, —$SO_2NR^y{}_2$; —CNO, —$NR^ySO_2R^y$, —NCO, —$N_3$, —$SiR^y{}_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur, where two or more $R^d$ groups may be taken together to form one or more optionally substituted rings, each $R^y$ is independently hydrogen, an optionally substituted group selected the group consisting of acyl; carbamoyl, arylalkyl; 6- to 10-membered aryl; $C_{1-12}$ aliphatic; $C_{1-12}$ heteroaliphatic having 1-2 heteroatoms independently selected from the group consisting of nitrogen, oxygen, and sulfur; 5- to 10-membered heteroaryl having 1-4 heteroatoms independently selected from the group consisting of nitrogen, oxygen, and sulfur; 4- to 7-membered heterocyclic having 1-2 heteroatoms independently selected from the group consisting of nitrogen, oxygen, and sulfur; an oxygen protecting group; and a nitrogen protecting group; two $R^y$ on the same nitrogen atom are taken with the nitrogen atom to form an optionally substituted 4- to 7-membered heterocyclic ring having 0-2 additional heteroatoms independently selected from the group consisting of nitrogen, oxygen, and sulfur; and each $R^4$ is independently is a hydroxyl protecting group or R.

In some embodiments, the moiety

has the structure:

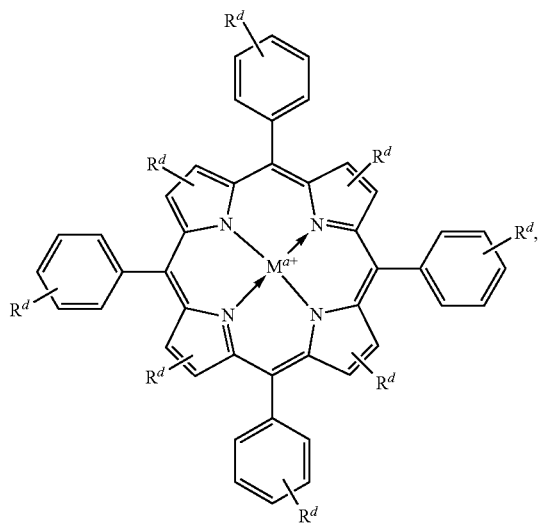

where M, a and $R^d$ are as defined above and in the classes and subclasses herein.

In some embodiments, the moiety

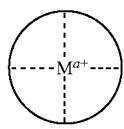

has the structure:

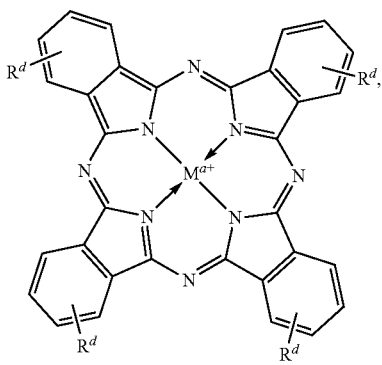

where M, a and $R^d$ are as defined above and in the classes and subclasses herein.

In some embodiments, Lewis acids included in heterogenous catalysts used in the processes described herein comprise metallo salenate complexes. In some embodiments, the moiety

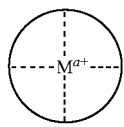

has the structure:

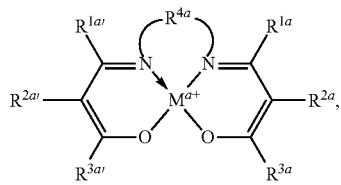

wherein:

M, and a are as defined above and in the classes and subclasses herein.

$R^{1a}$, $R^{2a}$, $R^{2a'}$, $R^{3a}$, and $R^{3a'}$ are independently hydrogen, halogen, —$OR^4$, —$NR^y_2$, —$SR^y$, —CN, —$NO_2$, —$SO_2R^y$, —$SOR^y$, —$SO_2NR^y_2$; —CNO, —$NR^ySO_2R^y$, —NCO, —$N_3$, —$SiR^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur; wherein each $R^4$, and $R^y$ is independently as defined above and described in classes and subclasses herein, wherein any of ($R^{2a'}$ and $R^{3a'}$), ($R^{2a}$ and $R^{3a}$), ($R^{1a}$ and $R^{2a}$), and ($R^{1a'}$ and $R^{2a'}$) may optionally be taken together with the carbon atoms to which they are attached to form one or more rings which may in turn be substituted with one or more $R^y$ groups; and $R^{4a}$ is selected from the group consisting of:

e)

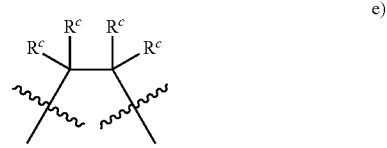

f)

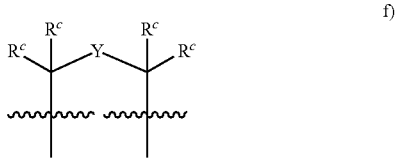

g)

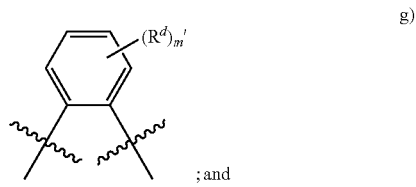

; and h)

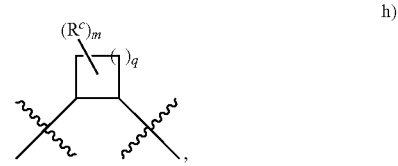

where $R^c$ at each occurrence is independently hydrogen, halogen, —$OR^4$, —$NR^y_2$, —$SR^y$, —CN, —$NO_2$, —$SO_2R^y$, —SOR$^y$, —SO$_2$NR$^y_2$; —CNO, —NR$^y$SO$_2$R$^y$, —NCO, —N$_3$, —SiR$^y_3$; or an optionally substituted group selected from the group consisting of C$_{1-20}$ aliphatic; C$_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur;

wherein:

two or more R$^c$ groups may be taken together with the carbon atoms to which they are attached and any intervening atoms to form one or more rings;

when two R$^c$ groups are attached to the same carbon atom, they may be taken together along with the carbon atom to which they are attached to form a moiety selected from the group consisting of: a 3- to 8-membered spirocyclic ring, a carbonyl, an oxime, a hydrazone, an imine; and an optionally substituted alkene;

where R$^4$ and R$^y$ are as defined above and in classes and subclasses herein;

Y is a divalent linker selected from the group consisting of: —NR$^y$—, —N(R$^y$)C(O)—, —C(O)NR$^y$—, —O—, —C(O)—, —OC(O)—, —C(O)O—, —S—, —SO—, —SO$_2$—, —C(=S)—, —C(=NR$^y$)—, —N=N—; a polyether; a C$_3$ to C$_8$ substituted or unsubstituted carbocycle; and a C$_1$ to C$_8$ substituted or unsubstituted heterocycle;

m' is 0 or an integer from 1 to 4, inclusive;

q is 0 or an integer from 1 to 4, inclusive; and x is 0, 1, or 2.

In some embodiments, a provided Lewis acid comprises a metallo salen compound, as shown in formula Ia:

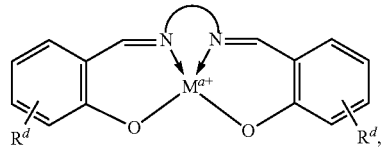

Ia wherein each of M, R$^d$, and a, is as defined above and in the classes and subclasses herein,

represents is an optionally substituted moiety linking the two nitrogen atoms of the diamine portion of the salen ligand, where

is selected from the group consisting of a C$_3$-C$_{14}$ carbocycle, a C$_6$-C$_{10}$ aryl group, a C$_3$-C$_{14}$ heterocycle, and a C$_5$-C$_{10}$ heteroaryl group; or an optionally substituted C$_2$-20 aliphatic group, wherein one or more methylene units are optionally and independently replaced by —NR$^y$—, —N(R$^y$)C(O)—, —C(O)N(R$^y$)—, —OC(O)N(R$^y$)—, —N(R$^y$)C(O)O—, —OC(O)O—, —O—, —C(O)—, —OC(O)—, —C(O)O—, —S—, —SO—, —SO$_2$—, —C(=S)—, —C(=NR$^y$)—, —C(=NOR$^y$)— or —N=N—.

In some embodiments metal complexes having formula Ia above, at least one of the phenyl rings comprising the salicylaldehyde-derived portion of the metal complex is independently selected from the group consisting of:

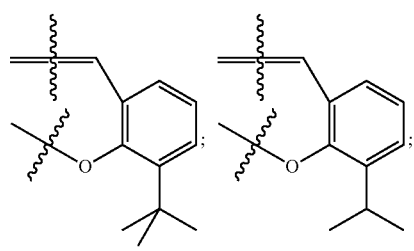

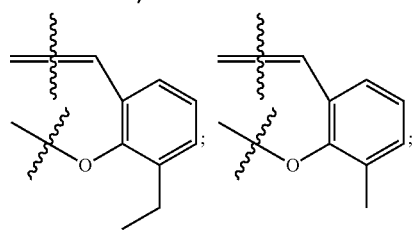

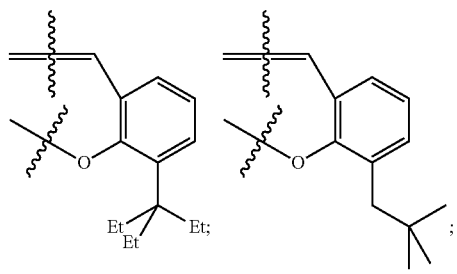

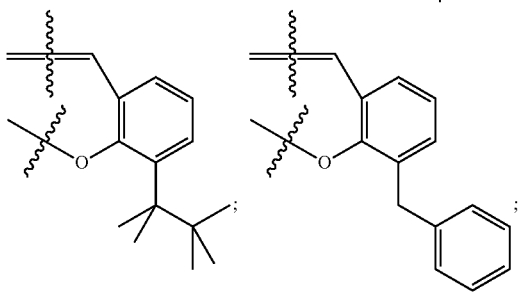

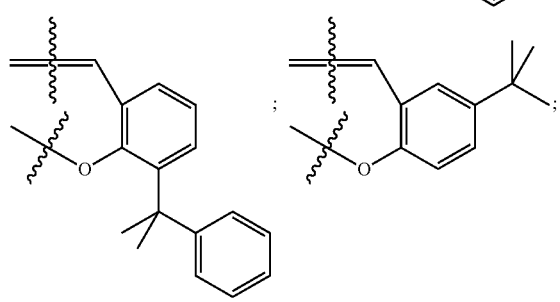

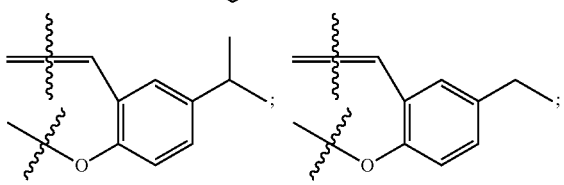

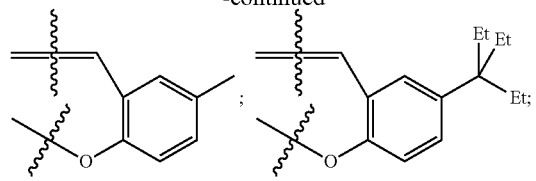
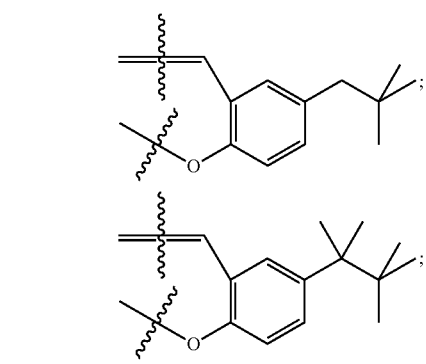
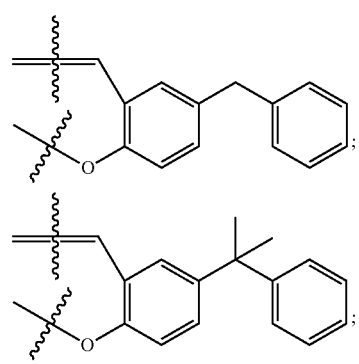
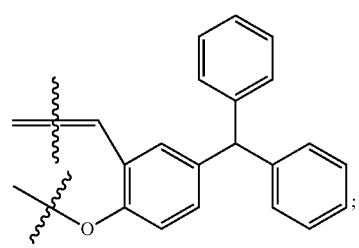
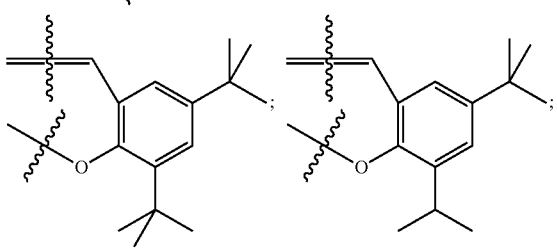
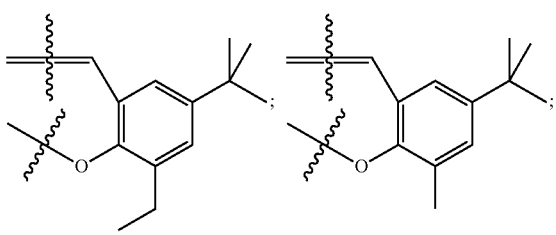
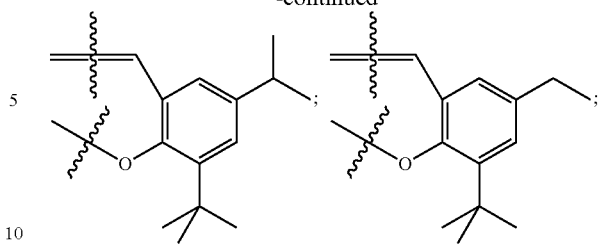
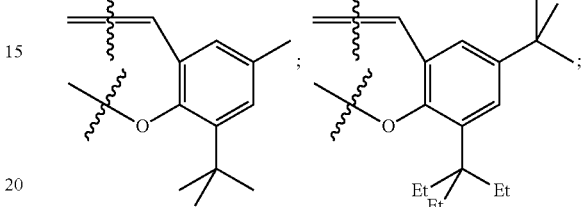
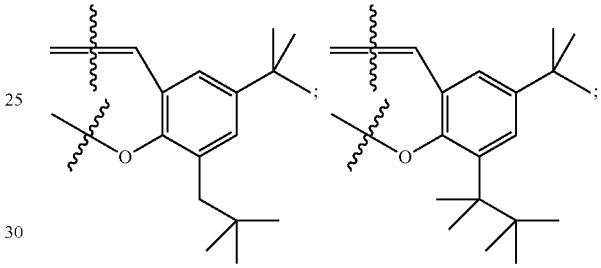
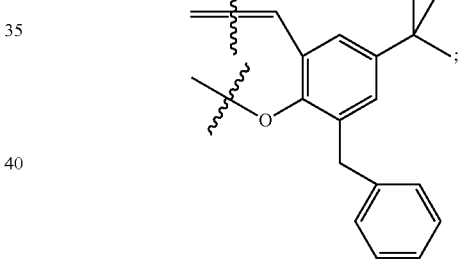
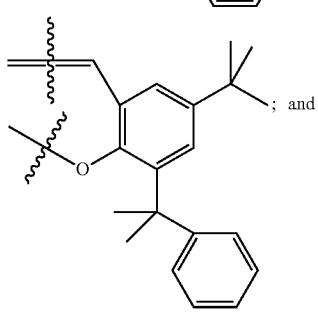
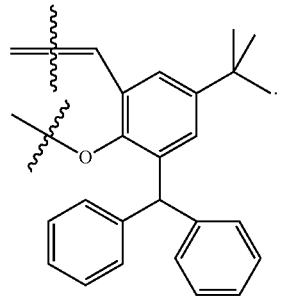

In some embodiments, a provided Lewis acid comprises a metallo salen compound, conforming to one of formulae Va or Vb:

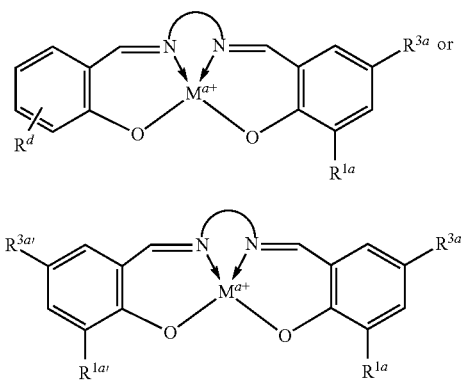

wherein M, a, $R^d$, $R^{1a}$, $R^{3a}$, $R^{1a'}$, $R^{3a'}$, and

are as defined above and in the classes and subclasses herein.

In some embodiments of metal complexes having formulae Va or Vb, each $R^{1a}$ and $R^{3a}$ 's, independently, optionally substituted $C_1$-$C_{20}$ aliphatic.

In some embodiments, the moiety

comprises an optionally substituted 1,2-phenyl moiety.

In some embodiments, Lewis acids included in heterogenous catalysts used in processes described herein comprise metal-tmtaa complexes. In some embodiments, the moiety

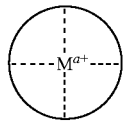

has the structure:

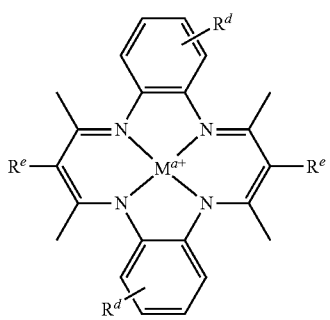

wherein M, a and $R^d$ are as defined above and in the classes and subclasses herein, and $R^e$ at each occurrence is independently hydrogen, halogen, —OR, —NR$^y_2$, —SR$^y$, —CN, —NO$_2$, —SO$_2$R$^y$, —SOR$^y$, —SO$_2$NR$^y_2$; —CNO, —NR$^y$SO$_2$R$^y$, —NCO, —N$_3$, —SiR$^y_3$; or an optionally substituted group selected from the group consisting of $C_{1-20}$ aliphatic; $C_{1-20}$ heteroaliphatic having 1-4 heteroatoms independently selected from the group consisting of nitrogen, oxygen, and sulfur; 6- to 10-membered aryl; 5- to 10-membered heteroaryl having 1-4 heteroatoms independently selected from nitrogen, oxygen, and sulfur; and 4- to 7-membered heterocyclic having 1-2 heteroatoms independently selected from the group consisting of nitrogen, oxygen, and sulfur.

In some embodiments, the moiety

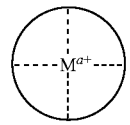

has the structure:

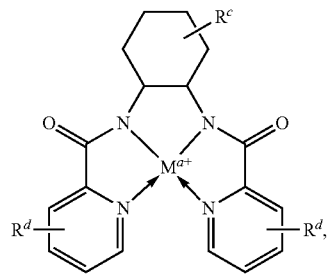

wherein each of M, a, $R^c$ and $R^d$ is as defined above and in the classes and subclasses herein.

In some embodiments, heterogenous catalysts used in systems and methods described herein may include a Lewis acidic metal complex. The metal atom may be selected from the periodic table groups 2-13, inclusive. In some embodiments, M may be a transitional metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium.

In some embodiments, M has an oxidation state of +2. In some embodiments, M is Zn(II), Cu(II), Mn(II), Co(II), Ru(II), Fe(II), Co(II), Rh(II), Ni(II), Pd(II) or Mg(II). In some embodiments M is Zn(II). In some embodiments, M is Cu(II).

In some embodiments, M has an oxidation state of +3. In some embodiments, M is Al(III), Cr(III), Fe(III), Co(III), Ti(III) In(III), Ga(III) or Mn(III). In some embodiments M is Al(III). In some embodiments, M is Cr(III).

In some embodiments, M has an oxidation state of +4. In some embodiments, M is Ti(IV) or Cr(IV).

In some embodiments, $M^1$ and $M^2$ are each independently a metal atom selected from the periodic table groups 2-13, inclusive. In some embodiments, M is a transition metal selected from the periodic table groups 4, 6, 11, 12 and 13. In some embodiments, M is aluminum, chromium, titanium, indium, gallium, zinc cobalt, or copper. In some embodiments, M is aluminum. In other embodiments, M is chromium. In some embodiments, $M^1$ and $M^2$ are the same. In some embodiments, $M^1$ and $M^2$ are the same metal, but have different oxidation states. In some embodiments, $M^1$ and $M^2$ are different metals.

In some embodiments, one or more of $M^1$ and $M^2$ may have an oxidation state of +2. In some embodiments, $M^1$ is Zn(II), Cu(II), Mn(II), Co(II), Ru(II), Fe(II), Co(II), Rh(II), Ni(II), Pd(II) or Mg(II). In some embodiments $M^1$ is Zn(II). In some embodiments $M^1$ is Cu(II). In some embodiments, $M^2$ is Zn(II), Cu(II), Mn(II), Co(II), Ru(II), Fe(II), Co(II), Rh(II), Ni(II), Pd(II) or Mg(II). In some embodiments $M^2$ is Zn(II). In some embodiments $M^2$ is Cu(II).

In some embodiments, one or more of $M^1$ and $M^2$ has an oxidation state of +3. In some embodiments, $M^1$ is Al(III), Cr(III), Fe(III), Co(III), Ti(III) In(III), Ga(III) or Mn(III). In some embodiments $M^1$ is Al(III). In some embodiments $M^1$ is Cr(III). In some embodiments, $M^2$ is Al(III), Cr(III), Fe(III), Co(III), Ti(III) In(III), Ga(III) or Mn(III). In some embodiments $M^2$ is Al(III). In some embodiments $M^2$ is Cr(III).

In some embodiments, one or more of $M^1$ and $M^2$ has an oxidation state of +4. In some embodiments, $M^1$ is Ti(IV) or Cr(IV). In some embodiments, $M^2$ is Ti(IV) or Cr(IV).

In some embodiments, the metal-centered Lewis-acidic component of the heterogenous catalyst may include a dianionic tetradentate ligand. In some embodiments, the dianionic tetradentate ligand is selected from the group consisting of: porphyrin derivatives; salen derivatives; dibenzotetramethyltetraaza[14]annulene (tmtaa) derivatives; phthalocyaninate derivatives; and derivatives of the Trost ligand. In some embodiments, the tetradentate ligand may be bound to siliceous material and/or tethered to the siliceous material by one or more other molecules.

In some embodiments, the heterogenous catalyst includes a carbonyl cobaltate in combination with an aluminum porphyrin compound. In some embodiments, the heterogenous catalyst is [(TPP)Al(THF)$_2$][Co(CO)$_4$] where TPP stands for tetraphenylporphyrin and THF stands for tetrahydrofuran.

In certain preferred embodiments, the heterogenous catalyst includes a carbonyl cobaltate in combination with a chromium porphyrin compound.

In some embodiments, the heterogenous catalyst includes a carbonyl cobaltate in combination with a chromium salen compound. In some embodiments, the heterogenous catalyst includes a carbonyl cobaltate in combination with a chromium salophen compound.

In some embodiments, the heterogenous catalyst includes a carbonyl cobaltate in combination with a metal salen compound. In certain embodiments, the metal salen compound is an aluminum salen compound. In some embodiments, the heterogenous catalyst includes a carbonyl cobaltate in combination with a metal salophen compound. In certain embodiments, the metal salophen compound is an aluminum salophen compound.

In some embodiments, one or more neutral two electron donors coordinate to M, $M^1$ or $M^2$ and fill the coordination valence of the metal atom. In some embodiments, the neutral two electron donor is a solvent molecule. In some embodiments, the neutral two electron donor is an ether. In some embodiments, the neutral two electron donor is tetrahydrofuran, diethyl ether, acetonitrile, carbon disulfide, or pyridine. In some embodiments, the neutral two electron donor is tetrahydrofuran. In some embodiments, the neutral two electron donor is an epoxide. In some embodiments, the neutral two electron donor is an ester or a lactone.

In certain embodiments, the heterogenous catalyst includes a carbonyl cobaltate in combination with an aluminum porphyrin compound and a solid support. In certain embodiments, the heterogenous catalyst includes a carbonyl cobaltate in combination with a chromium porphyrin compound and a solid support. In certain embodiments, the heterogenous catalyst includes a carbonyl cobaltate in combination with a chromium salen compound and a solid support. In certain embodiments, the heterogenous catalyst includes a carbonyl cobaltate in combination with a chromium salophen compound and a solid support. In certain embodiments, the heterogenous catalyst includes a carbonyl cobaltate in combination with an aluminum salen compound and a solid support. In certain embodiments, the heterogenous catalyst includes a carbonyl cobaltate in combination with an aluminum salophen compound and a solid support.

In certain preferred embodiments, the heterogenous catalyst of the present invention includes a solid support such as a structured zeolite. In certain embodiments, the heterogenous catalyst includes a cationic Lewis acid functional group and/or an anionic metal carbonyl supported by a structured zeolite. In a further embodiment, the structured zeolite has a faujasite, mordenite, or ZSM-5 (MFI) structure. In a further embodiment, the structure has the hexagonal pore arrangement of MCM-41. In a further embodiment, the structure has the cubic pore arrangement of MCM-48. In a further embodiment, the structure has the lamellar pore arrangement of MCM-50. In a further embodiment, the structure has pores organized in a foam arrangement. In a further embodiment, the structure has randomly placed pores. In a further embodiment, the structured zeolite material is Y[MCM-41], MOR[MCM-41], or ZSM-5[MCM-41]. In a further embodiment, the mean pore diameter within the structure is about 2 to about 5 nm. In a further embodiment, the mean pore diameter within the structure is about 2 to about 3 nm. In a further embodiment, the wall thickness within the structure is about 1 to about 5 nm. In a further embodiment, the wall thickness within the structure is about 1 to about 3 nm.

The synthesis of fully crystalline structured zeolites is applicable to a wide variety of materials. The first strategy is based on the short-range reorganization of a zeolite structure in the presence of a surfactant to accommodate mesoporosity without loss of zeolitic full crystallinity. A zeolite is added to a pH controlled solution containing a surfactant. Alternatively, a zeolite is added to a pH controlled solution and thereafter a surfactant is added. The pH controlled solution can be, for example, a basic solution with a pH ranging from about 8 to about 12, or from about 9 to about 11, or alternatively, the basic solution pH can be about 10. The strength of the base and the concentration of the basic solution are selected to provide a pH within the desired range. Any suitable base can be employed that falls within the desired pH range.

A charged chemical species, for example a positively charged chemical species, can be anchored to the fully crystalline structure. The charged chemical species can be cations of an element, quaternary amines, ammonium ions, pyridinium ions, or phosphonium ions, or any combination thereof. Alternatively, a chemical species can be anchored and/or covalently bonded to the fully crystalline structure. The chemical species can be a basic chemical species, an inorganic base, an organic base, hydroxide, amine, pyridine, or phosphine, or any combination thereof.

In certain embodiments, the heterogenous catalyst includes a solid support that comprises a siliceous based material, e.g., silica, and/or a carbon based material, e.g., carbon black or activated carbon, although any of a variety of other suitable supporting materials may be used. In some embodiments, the heterogenous catalyst may comprise a material selected from the group comprising silica, alumina, titania, silica/alumina, pyrogenic silica, high purity silica, zirconia, carbon (e.g., carbon black or activated carbon), zeolites and mixtures thereof. In some embodiments, the heterogenous catalyst comprises a siliceous material such as silica, pyrogenic silica, or high purity silica. In some embodiments, the siliceous material is substantially free of alkaline earth metals, such as magnesium and calcium.

In certain preferred embodiments, the heterogeneous catalyst comprises a cationic Lewis acid functional group and/or an anionic metal carbonyl supported on a heterogenous solid support formed by contacting the support material and the cationic Lewis acid functional group and/or the anionic metal carbonyl by a method such as physical mixture, dry impregnation, wet impregnation, incipient wet impregnation, ion-exchange, and vaporization.

In some embodiments, at least one metal complex may be impregnated into a heterogenous solid support. With impregnation, the at least one metal complex and heterogenous solid support material are mixed together followed by drying and calcination to form the heterogenous catalyst. With simultaneous impregnation, it may be desired to employ a dispersion agent, surfactant, or solubilizing agent, e.g., ammonium oxalate or an acid such as acetic or nitric acid, to facilitate the dispersing or solubilizing of the first, second and/or optional third metal complex in the event one or more of the metal complexes are incompatible.

In certain embodiments, sequential impregnation may be used to form the heterogenous catalyst. With sequential impregnation, a first metal complex may be first added to a heterogenous solid support material followed by drying and calcining, and the resulting material may then be impregnated by subsequent one or more metal complex followed by an additional drying and calcining to form the final heterogenous catalyst. In some embodiments, additional metal complexes may be added either with the first and/or second metal complex or in a separate sequential impregnation, followed by drying and calcination. In some embodiments, combinations of sequential and simultaneous impregnation may be employed if desired.

The inorganic solid oxides comprise specified large, intermediate or small pore zeolites having generally pore dimensions smaller than about 10 Å (see "Introduction to Zeolite Science and Practice", H. Van Bekkum et al., Studies in Science and Catalysis, No. 58, p. 632 and U.S. Pat. No. 5,256,828), or one or more oxides of compounds selected from Group IV of the Periodic Table. Zeolite materials which can be used as suitable matrices include certain small pore faujasites, medium pore pentasils, the small pore ferrierite, the two-dimensional large pore mordenite, large pore p-type materials and basic zeolites. Basic zeolites which are particularly effective in the instant invention are large pore X and Y zeolites, particularly the sodium form, e.g. NaX, NaY, zeolite L in potassium form (KL) and synthetic ferrierite. Also suitable are oxides of Groups III and/or IV, including oxides of aluminum, silica, titanium, zirconium, hafnium, germanium, tin and lead, as well as mixtures thereof. Particularly preferred ore oxides of aluminum and silica and mixtures thereof.

Medium pore, pentasil-type zeolites having 10-membered oxygen ring systems include, for example, ZSM-5, ZSM-11, ZSM-22, ZSM-23, ZSM-48 and laumontite. Their framework structures contain 5-membered oxygen rings and they are more siliceous than previously known zeolites. In many instances these zeolites may be synthesized with a predominance of silicon and with only a very small concentration of other atoms such as aluminum; thus, these zeolites may be considered as "silicates" with framework substitution by small quantities of other elements such as aluminum. Among the zeolites in this group, only ZSM-5 and ZSM-11 have bidirectional intersecting channels, the others have nonintersecting unidirectional channels.

The medium-pore pentasils, unlike other zeolites, have pores of uniform dimension and have no large supercages with smaller size windows. This particular feature is believed to account for their unusually low coke-forming propensity in acid-catalyzed reactions. Because the pentasil zeolites are devoid of the bottle-necks in the window/cage structure, molecules larger than the size of the channel do not form with the exception perhaps at the intersections.

Properties of ZSM-5 which are of significance to shape-selective catalysis are the presence of two intersecting channels formed by rings of 10 oxygen atoms. The two intersecting channels, both formed by 10-membered oxygen rings, are slightly different in their pore size. One runs parallel to the a-axis of the unit cell; it is sinusoidal and has a nearly circular (5.4×5.6 Å) opening. The other runs parallel to the b-axis and has a straight, but elliptical opening (5.1×5.5 Å). See W. M. Meier and D. H. Olson, Atlas of Zeolite Structure Types, International Zeolite Assoc., Polycrystal Book Service, Pittsburgh, 1978.

Also very useful are zeolites having dual pore systems displaying interconnecting channels of either 12- and 8-membered oxygen ring openings or 10- and 8-membered oxygen ring openings. Examples are mordenite, offretite, Linde T, gmelinite, heuliandite/clinoptilolite, ferrierite, ZSM-35, -38, stilbite, dachiardite, epistilbite, etc. Because the smaller channels are accessible only by the smaller molecules while the larger channels are accessible by both the large and small molecules, their catalytic properties are sometimes quite distinct from other zeolites. However, most of the natural varieties and some of the synthetic samples contain numerous stacking faults, and in many catalytic reactions they behave like small-pore zeolites. The test runs in Example 2 demonstrate the usefulness of ferrierite and mordenite.

The preferred zeolites may have dual pore systems and/or pore dimensions of about 3 to 8 Å. Specific examples of preferred supports include the pentasil ZSM-5, ferrierite, mordenite and the Y-zeolite in sodium form (NaY) in addition to alumina, silica/alumina and zeolite alumina.

The desired metals can be introduced onto the solid support by either ion exchange or impregnation. In ion exchange, metal ions can be introduced into zeolites by direct exchange of a cation into the structure from aqueous solutions of their salts such as nitrates, chlorides, acetates and the like.

Impregnation is used in the instant invention. The metal compounds may be dissolved in a suitable solvent such as, for example, water, aqueous ammonia, dilute phosphoric acid or others. The alkali compound may be associated with the catalyst rather than a replacement of cation by cation in the exchange procedure.

The quantity of alkali metal, alkaline earth metal or alkali metal halide exchanged or impregnated into the inorganic solid oxide may vary. The reaction proceeds when employing as little as about one to 50% of said compound together with about 50 to 99 wt % zeolite or Group IV oxide, basis the total weight of the catalyst. Optionally said alkali or alkaline earth-treated zeolite or Group IV oxide may be calcined at 100°-800° C.

The temperature range which can usefully be employed is variable depending upon other experimental factors, including pressure and choice of particular species of catalysts, among other things. The range of operability is from about 80° to 200° C. A narrow range of 130° to 170° C. is preferred. The examples demonstrate that the most preferred temperature is about 140° C.

Pressures of atmospheric to 100 psig can be used. In most instances very mild pressures of about 50 psig are sufficient.

The novel catalyst can typically be introduced into an autoclave initially and the reactants can be continuously or intermittently introduced into such a zone during the course of the reaction.

The products have been identified by gas and liquid chromatography.

Various embodiments of the process of this invention are demonstrated in the following examples which are only intended to be illustrative and are not intended to limit the invention in any way.

EXAMPLES

Several acronyms and abbreviations are used throughout this section. For clarity, the most commonly used are presented here. Ethylene Oxide ("EO"); Carbon Monoxide ("CO"); Propylene Oxide ("PO"); Turnover Frequency ("TOF"); Propiolactone or beta-Propiolactone ("PL"); Butyrolactone or beta-Butyrolactone ("BBL"); concentrations are indicated with brackets, e.g., concentration of Propiolactone [PL]; Freeze-Pump-Thaw ("FPT").

Example 1: Heterogeneous Catalyst

The use of ZSM-5 pentasil zeolite (from Conteka) which is impregnated with 20 wt % KOH and calcined at 530° C. for five hours, as a solid support. A dried sample of ZSM-5 (103 g) is charged into a 500 mL 3-neck round bottom flask equipped with an inert gas inlet, a gas outlet, and a scrubber containing aqueous sodium hydroxide solution. A solution containing 143 g n-heptane (99+%; <50 ppm water) and [(CITPP)Al][Co(CO)$_4$] is added to the flask under a dry inert gas atmosphere. The mixture is mixed well by swirling. Solvent is removed using a rotary evaporator at 80° C. and 5-10 mbar pressure.

A portion of the dried impregnated ZSM-5 thereby obtained is charged into a tubular quartz reactor (1 inch ID, 16 in long) equipped with a thermowell, a 500 mL 3-neck round bottom flask, a heating mantle, an inert gas inlet and a scrubber (containing aqueous sodium hydroxide). The bed of impregnated zeolite ZSM-5 is heated to 850° C. under dry nitrogen (99.999% purity) flow (400 cc/min). After the bed temperature has been at 850° C. for 30 minutes, the power to the furnace is turned off and the catalyst bed is cooled down to 400° C.

Water (5.0 g) is then added to the 3-neck round bottom flask and the contents of the flask heated with a heating mantle to reflux while maintaining a N$_2$ flow of 400 cc/min. The water is distilled through the catalyst bed over a period of 30 minutes, with a heat gun being used to heat the round-bottom flask to ensure that all residual water has been driven out of the flask and through the catalyst bed. After maintaining the bed at 400° C. for an additional 2 hours, the tube reactor is permitted to cool to room temperature.

Example 2: Conversion of Ethylene Epoxide to β-Propiolactone

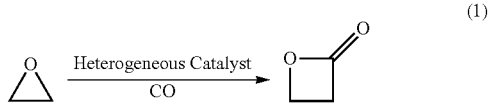
(1)

A 300 mL Parr reactor is dried overnight under vacuum. In a nitrogen glovebox, the reactor is charged with [(CITPP)Al][Co(CO)$_4$] (66 mg, 60 mmol) on a solid support, such as ZSM-5 (1 g), hexamethylbenzene (162 mg, 1.0 mmol), and THF (dried over 4 Å molecular sieves, and freeze, pump, and thaw 3 times), then closed and removed from the glovebox. Ethylene oxide is vacuum transferred to a transfer vessel from EO lecture bottle. The Parr reactor is cooled to −78° C. and high vacuum is applied to the reactor. The vacuum is disconnected from the reactor, and the transfer vessel is connected to the Parr reactor to allow EO to be vacuum transferred from the transfer vessel to the reactor at −78° C. The reaction mixture is warmed to ambient temperature and saturated with CO by pressurizing the reactor with CO to three fourth of the desired CO pressure (e.g. 150 psi), then heated to the desired temperature. After the temperature of reaction mixture reaches the desired temperature, the reactor is pressurized to the desired pressure (e.g. 200 psi). The reaction mixture is agitated for 3 h. The reactor is cooled to <0° C. and vented. A portion of reaction mixture is sampled and analyzed by $^1$H NMR in CDCl$_3$.

Temperature and pressure effect on carbonylation of EO is studied by varying the temperature and pressure.

TABLE 2

Temperature and pressure effect on catalyst activity in THF

| Temp rxn # | pressure (° C.) | yield (%) (psi) | EO$^c$ | Ald.$^c$ | PL$^c$ | SA$^c$ |
|---|---|---|---|---|---|---|
| 29-39$^a$ | 30 | 200 | 69 | 0 | 22 | 0 |
| 29-56$^b$ | 60 | 200 | 0.4 | 5 | 92 | 0.1 |
| 29-59$^b$ | 30 | 600 | 44 | 0 | 44 | 0 |
| 29-54$^b$ | 60 | 600 | 0 | 0 | 88 | 8 |
| 29-57$^b$ | 60 | 600 | 0 | trace | 81 | 13 |
| 29-66$^b$ | 45 | 400 | 25 | trace | 73 | 0 |

* Conditions: EO (1.8M; Arc), catalyst: [(CITPP)Al][Co(CO)$_4$] (60 μmol) on ZSM-5 (2.0 g), EO:cat = 1500:1, total volume: 50 mL (in THF), agitation speed: 730 rpm, reaction time: 3 h, and internal standard: hexamethylbenzene.
$^a$catalyst: hexamethylbenzene (0.5 mmol; Alfa Aesar (Ward Hill, MA), and THF (received from the column; FPT *2)
$^b$catalyst: hexamethylbenzene (1.0 mmol; TCI), and THF (dried over 4 Å sieves and stored in the glove box; FPT *2)
$^c$EO (ethylene oxide), Ald. (acetaldehyde), PL (propiolactone), and SA (succinic anhydride)

A pressure increase from 200 psi of CO to 600 psi at 30° C. doubles the yield of propiolactone (see 29-39 and 29-59 in Table 2). When the reaction temperature is increased from 30° C. to 60° C. at 200 psi of CO (see 29-39 and 29-54), the reaction goes to completion and the yield of propiolactone more than triples.

Reaction Procedure A—The reaction procedure for carbonylation of ethylene oxide in THF is as follows:

TABLE 3

Reaction time and catalyst loading (30° C.; 200 psi CO)

| rxn # | time (h) | cat. (mmol) | EO/cat | yield (%) EO | TOF Ald. | PL | SA | (/h) |
|---|---|---|---|---|---|---|---|---|
| 29-39 | 3 | 0.06 | 1500 | 69 | 0 | 22 | 0 | 110 |
| 29-38 | 6 | 0.06 | 1500 | 63 | 0 | 28 | 0 | 70 |
| 29-43 | 3 | 0.12 | 750 | 60 | 0 | 32 | 0 | 80 |

* Conditions: EO (1.8M), catalyst: [(ClTPP)Al][Co(CO)$_4$] (60 μmol) on ZSM-5 (2.0 g), EO:cat = 1500:1, total volume: 50 mL (in THF), agitation speed: 730 rpm, reaction time: 3 h, internal standard: hexamethylbenzene (0.5 mmol; Alfa Aesar), and THF (received from the column; FPT *2)

Example 3: Conversion of Propylene Epoxide to β-Lactone

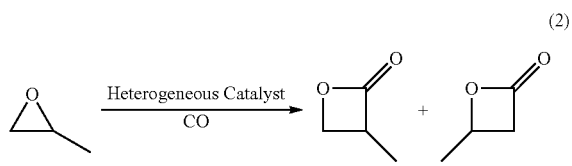

(2)

A representative Reaction Procedure for Carbonylation of Propylene Oxide is as follows:

A 300 mL Parr reactor is dried overnight under vacuum. In a nitrogen glovebox, the reactor is charged with [(ClTPP)Al][Co(CO)$_4$] (66 mg, 60 μmol) on ZSM-5 (4 g) and hexamethylbenzene (81 mg, 0.50 mmol), then closes and removes from the glovebox. Solvent is added via a syringe under N$_2$. The reaction mixture is saturated with CO by pressurizing the reactor with CO to about 15 psi. Propylene oxide (6.3 mL, 90 mmol) is added to the reactor via syringe. The reactor is pressurized with CO to three fourth of the desired CO pressure (e.g. 150 psi), then heated to the desired temperature. After the temperature of reaction mixture reaches the desired temperature, the reactor is pressurized to the desired pressure (e.g. 200 psi). The reaction mixture is agitated for 3 h. The reactor is cooled to <0° C. and vented. A portion of reaction mixture is sampled and analyzed by $^1$H NMR in CDCl$_3$.

Example 4: Catalyst Stability

Design of a continuous process for the carbonylation of epoxide to form propiolactone requires a catalyst which maintains activity for a significant amount of time. There are a number of factors which may influence the long-term stability of the catalyst, including temperature, solvent, impurities, and material compatibility.

A. Carbonylation:

The carbonylation reaction is shown in Scheme below. Coordination of an epoxide to the Lewis acid Al$^+$ center, followed by nucleophilic attack on the epoxide by the [Co(CO)$_4$]$^-$ anion leads to ring opening of the epoxide (2). CO insertion is typically swift to form the Co-acyl (3), which is the resting state of the catalyst in THF. Ring closing of the lactone is the rate determining step in THF, followed by loss of the lactone and coordination of another solvent molecule to reform the ion pair 1. At high temperatures and low CO concentrations, however, 2 can undergo β-hydrogen elimination to form a ketone molecule, which is a fast and exothermic reaction. In certain solvents, the lactone can undergo subsequent carbonylation to an anhydride molecule. This typically occurs at high temperatures and when the concentration of epoxide becomes very low. The formation of anhydride is also solvent dependent, being very fast in DBE, and almost non-existent in THF and sulfolane.

Scheme Carbonylation of epoxides with [ClTTP)Al]$^+$[Co(CO)$_4$]$^-$.

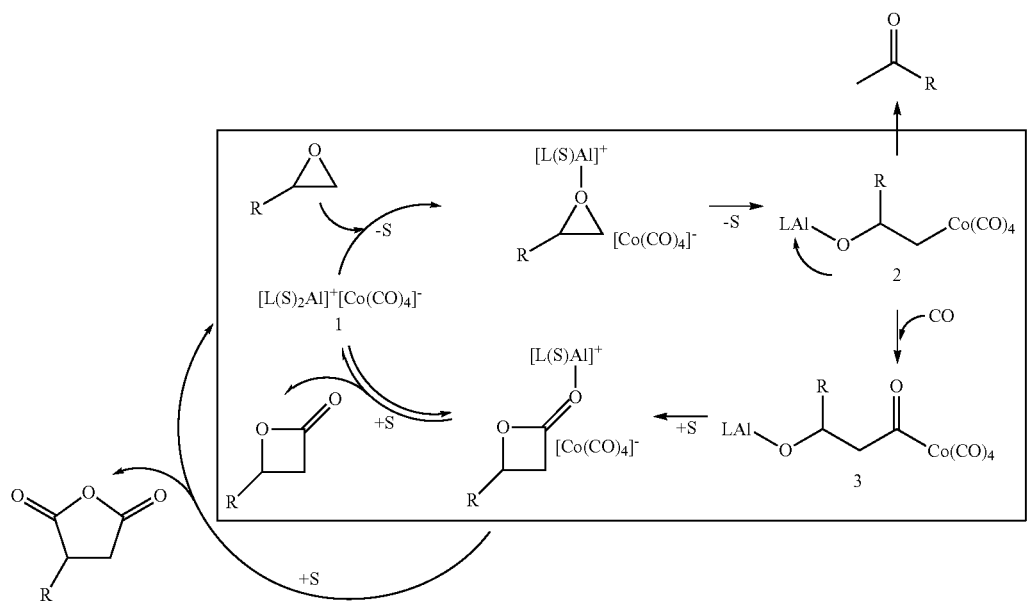

R=H, Me
S=Coordinative solvent, substrate, product

Example 5: Conversion of an Epoxide and Carbon Monoxide to β-Lactone

This Example demonstrates the representative production of β-lactone from an epoxide and carbon monoxide using a heterogeneous catalyst. Exemplary reaction schemes are shown below.

A 100 ml Parr reactor is dried at 90° C., under vacuum overnight. In a drybox, it is cooled in a −35° C. freezer for at least 1.5 hours and equipped with a small test-tube and magnetic stir bar. The test-tube is charged with 0.500 ml of epoxide, stored at −35° C., and [(ClTPP)Al][Co(CO)$_4$] on a solid support, such as ZSM-5 (MFI) (10 g). Upon removal from the drybox, the reactor is pressurized to pressure as 900 psi, placed in a preheated oil bath and the reactor is stirred at about 60° C. for about 4-10 hours. When the reaction time has passed, the reactor is cooled in a bath of dry ice/acetone until the pressure reached a minimum and then slowly vented. The crude mixture is subjected to NMR analysis. Trapping of vented gases indicates that only 2-5% of the material is lost. Vented gases contained the same ratios of compounds (within 3-4%) that remained in the reactor.

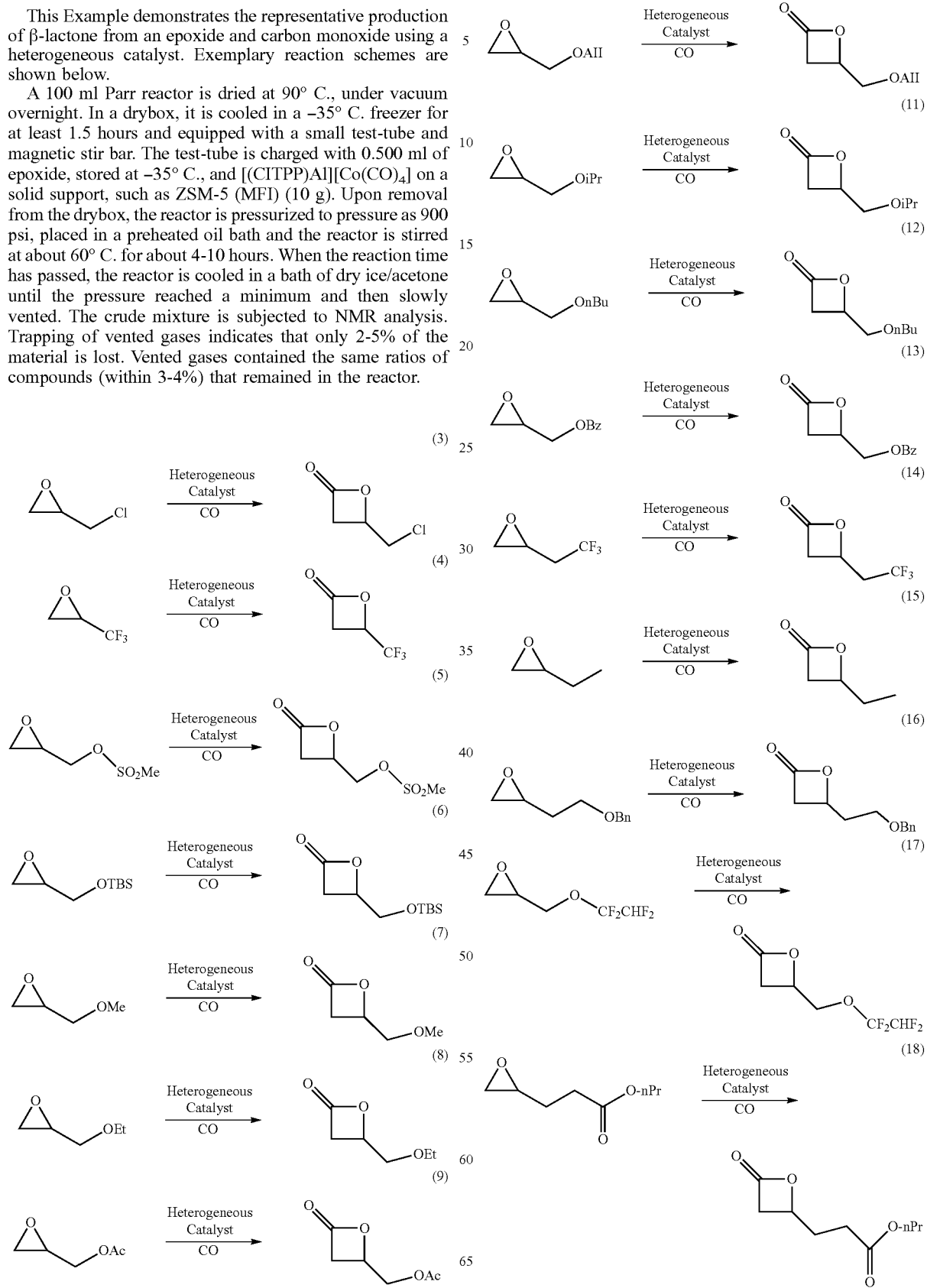

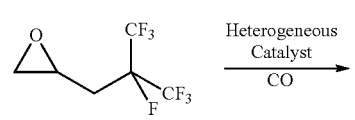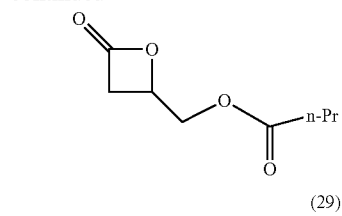
(19)
(20)
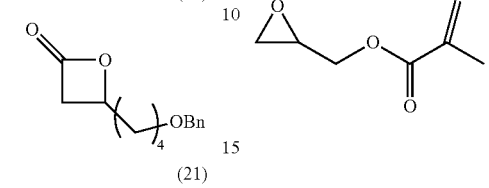
(21)
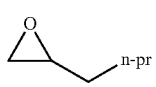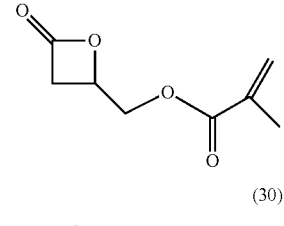
(22)
(30)
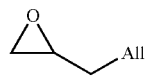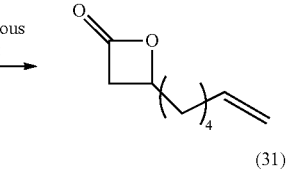
(23)
(31)
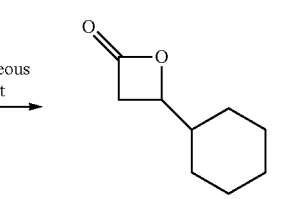
(24)
(32)
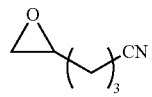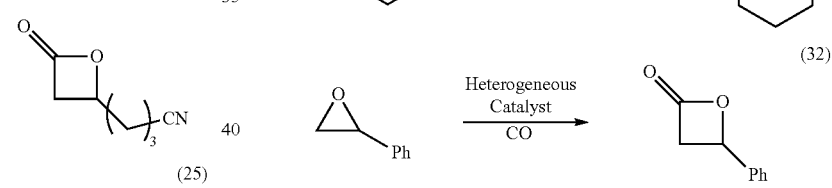
(25)
(33)
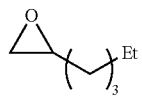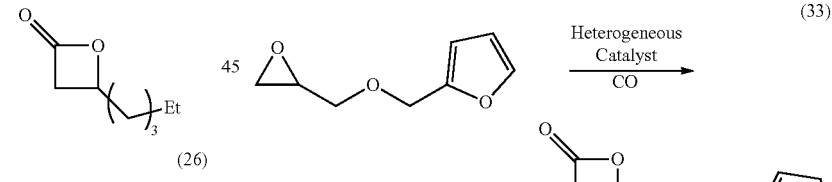
(26)
(34)
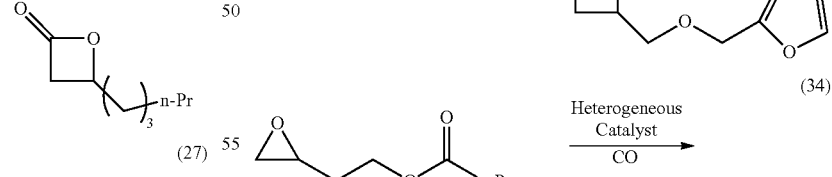
(27)
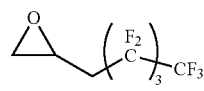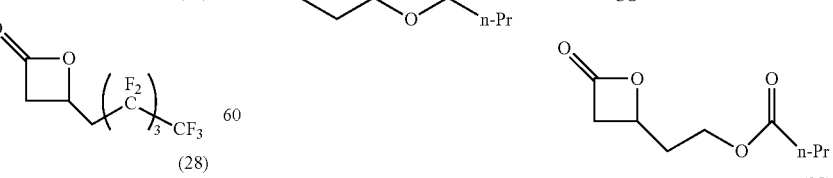
(28)
(35)
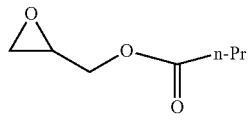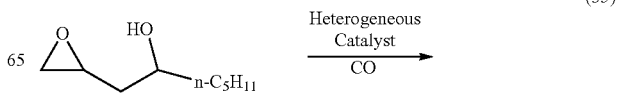

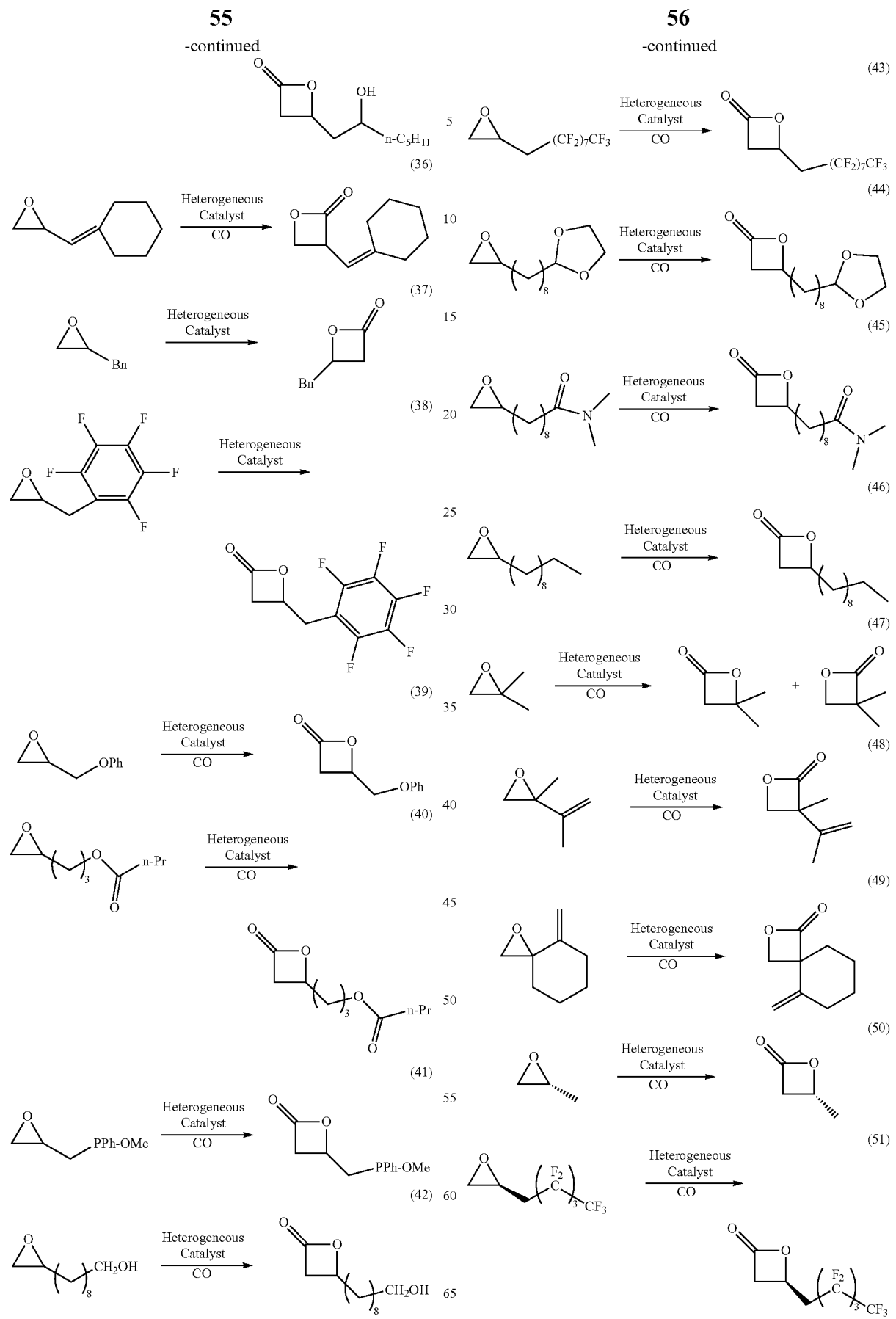

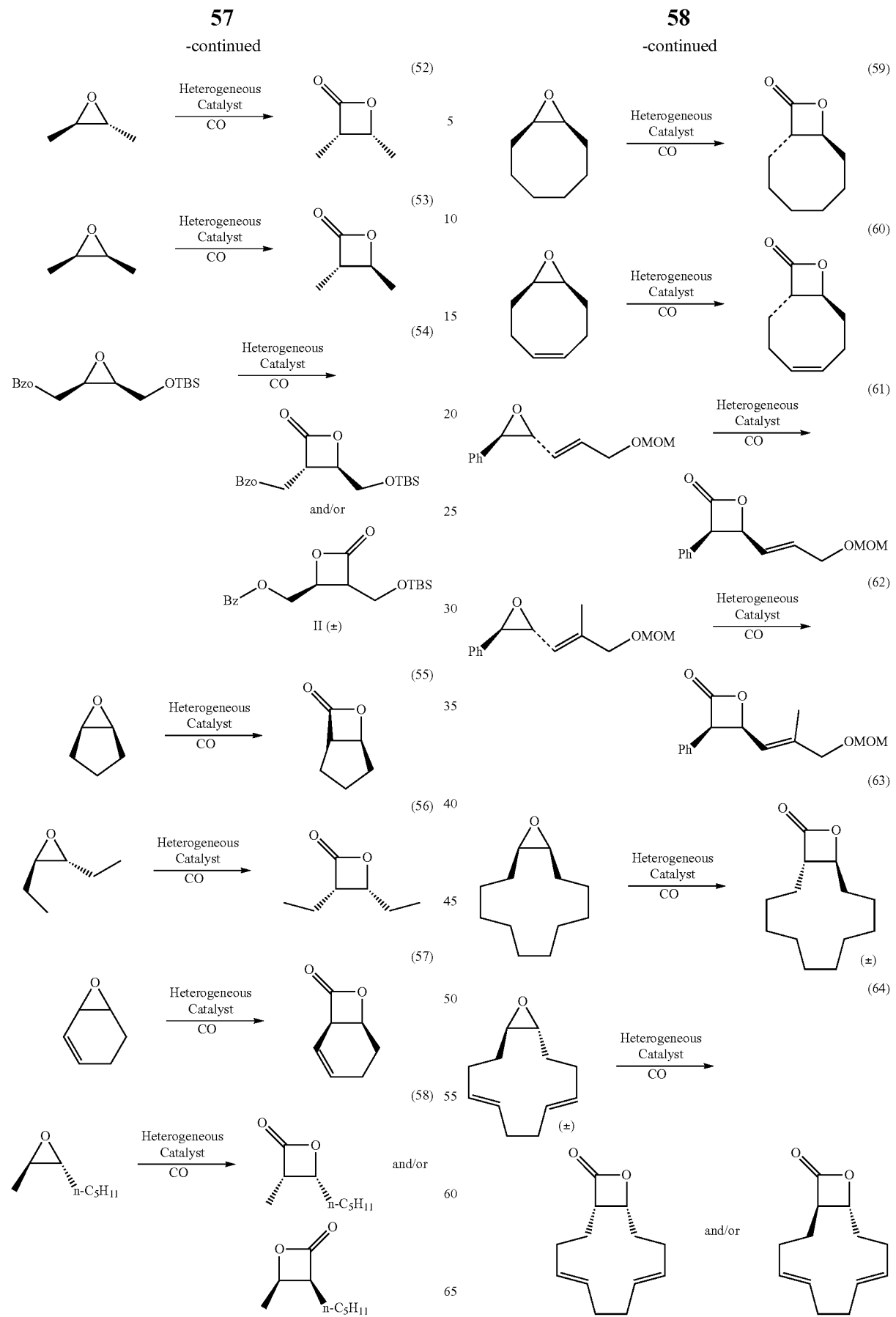

-continued

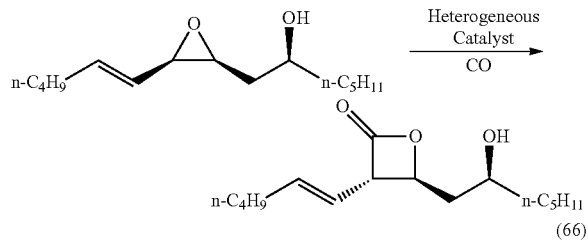
(65)

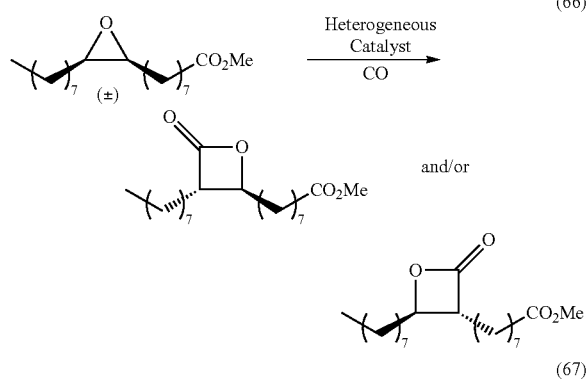
(66)
and/or
(67)

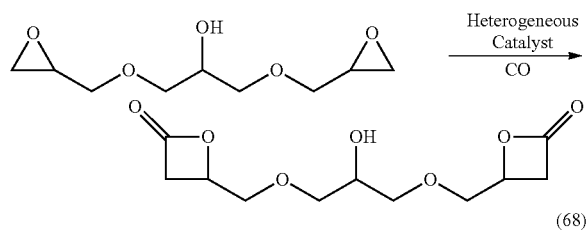
(68)

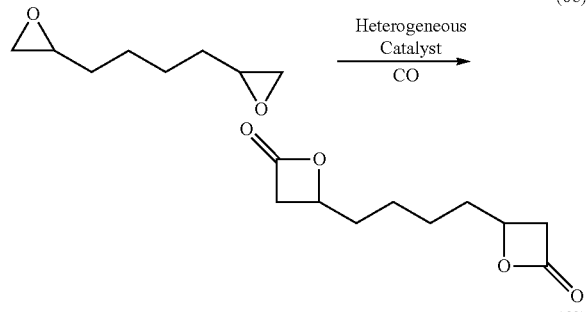
(69)

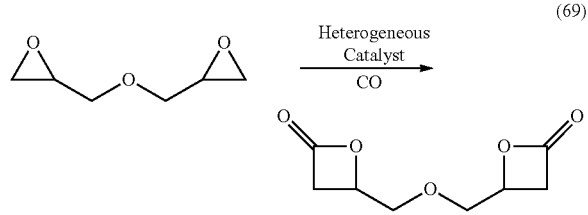

The embodiments described herein are not intended to be limited to the aspects shown, but are to be accorded the widest scope consistent with the principles and features disclosed herein.

What is claimed is:

1. A heterogeneous catalyst useful for producing beta-lactone from an epoxide reagent, a carbon monoxide reagent, and mixtures thereof in a carbonylation process, said heterogeneous catalyst comprising a solid component comprising a catalytically effective amount of cationic Lewis acid functional group and anionic metal carbonyl compound associated with a solid support and wherein the cationic Lewis acid functional group is anchored or covalently bonded to the solid support, wherein the heterogeneous catalyst further comprises from about 0.1 weight percent to about 10 weight percent cationic Lewis acid functional group and anionic metal carbonyl compound.

2. The heterogeneous catalyst of claim 1, wherein the heterogeneous catalyst further comprises from about 0.1 weight percent to about 2 weight percent each of cationic Lewis acid functional group and anionic metal carbonyl compound.

3. The heterogeneous catalyst of claim 1, wherein the anionic metal carbonyl compound is selected from a group consisting of $[Co(CO)_4]^-$, $[Ti(CO)_6]^{2-}$, $[V(CO)_6]^-$, $[Rh(CO)_4]^-$, $[Fe(CO)_4]^{2-}$, $[Ru(CO)_4]^{2-}$, $[Os(CO)_4]^{2-}$, $[Cr_2(CO)_{10}]^{2-}$, $[Fe_2(CO)_8]^{2-}$, $[Tc(CO)_5]^-$, $[Re(CO)_5]^-$, and $[Mn(CO)_5]$.

4. The heterogeneous catalyst of claim 1, wherein the catalytically effective amount of cationic Lewis acid functional group comprises at least one Lewis acidic metal complex selected from a group consisting of Zn(II), Cu(II), Mn(II), Co(II), Ru(II), Fe(II), Rh(II), Ni(II), Pd(II), Mg(II), Al(III), Cr(III), Fe(III), Co(III), Ga(III), Mn(III), Ti(IV) and Cr(IV).

5. The heterogeneous catalyst of claim 1, wherein the solid support is selected from a group consisting of silica, alumina, titania, silica/alumina, pyrogenic silica, high purity silica, zirconia, carbon black, activated carbon, metal halide, zeolite and the combination thereof.

6. The heterogeneous catalyst of claim 5, wherein the zeolite is selected from a group consisting of a faujasite structure, a mordenite structure, a ZSM-5 (MFI) structure, a hexagonal pore arrangement of MCM-41, a cubic pore arrangement.

7. A process for carbonylation using the heterogeneous catalyst of claim 1, wherein the process comprises the steps:
passing a feed stream comprising an epoxide reagent and a carbon monoxide reagent to a reaction zone;
contacting the epoxide reagent and the carbon monoxide reagent with the heterogeneous catalyst to produce a beta-lactone product in the reaction zone; and
removing the beta-lactone product from the reaction zone.

8. The process of claim 7, wherein the step for contacting the epoxide reagent and the carbon monoxide reagent with the heterogeneous catalyst to produce the beta-lactone product in the reaction zone is performed in a vapor phase.

9. The process of claim 7, wherein the step for contacting the epoxide reagent and the carbon monoxide reagent with the heterogeneous catalyst to produce the beta-lactone product in the reaction zone is performed in a liquid phase using a solvent.

10. The process of claim 9, wherein the process further comprises a distillation step to separate the beta-lactone product from the solvent.

11. The process of claim 7, wherein the process further comprises a step of contacting the epoxide reagent and the carbon monoxide reagent with the heterogeneous catalyst to produce a beta-lactone intermediate in the reaction zone.

12. The process of claim 11, wherein the process further comprises a step of polymerizing the beta-lactone intermediate in the reaction zone to produce a polylactone product.

13. The process of claim 11, wherein the process further comprises a step of reacting the beta-lactone intermediate with a derivative reagent in the reaction zone to produce a beta-lactone derivative.

14. The process of claim 13, wherein the derivative reagent is chosen from a list selected from the group consisting of a carbon monoxide reagent, a beta-lactone reagent, an ammonia reagent, and an alcohol reagent.

15. A process for making the heterogeneous catalyst of claim 1, wherein the process comprises the steps:
   impregnating a solid support with a solution comprising a Lewis acid functional group and a metal carbonyl compound in a non-oxygenated hydrocarbon solvent to form an impregnated solid support; and
   calcining the impregnated solid support to form the heterogeneous catalyst.

16. The process of claim 15, wherein the solid support comprises a crystalline structured zeolite.

17. The process of claim 16, wherein the process further comprises a step of mixing the Lewis acid functional group and the metal carbonyl compound with the crystalline structured zeolite.

18. The process of claim 17, wherein the process further comprises a step of drying and calcining at 100° C.-400° C.

* * * * *